United States Patent [19]

Moriyama

[11] Patent Number: 5,976,074
[45] Date of Patent: *Nov. 2, 1999

[54] ENDOSCOPE PROVIDED WITH FUNCTION OF BEING LOCKED TO FLEXIBILITY OF INSERTION PART WHICH IS SET BY FLEXIBILITY MODIFYING OPERATION MEMBER

[75] Inventor: Hiroki Moriyama, Yokohama, Japan

[73] Assignee: Olympus Optical Co., Ltd., Tokyo, Japan

[ * ] Notice: This patent is subject to a terminal disclaimer.

[21] Appl. No.: 09/114,419

[22] Filed: Jul. 6, 1998

Related U.S. Application Data

[63] Continuation of application No. 08/712,914, Sep. 12, 1996, Pat. No. 5,810,715.

[30] Foreign Application Priority Data

Sep. 29, 1995 [JP] Japan .................................... 7-253311
May 7, 1996 [JP] Japan .................................... 8-112637
Jun. 28, 1996 [JP] Japan .................................... 8-169722

[51] Int. Cl.[6] ...................................................... A61B 1/00
[52] U.S. Cl. .......................... 600/144; 600/139; 600/141; 600/146; 600/148
[58] Field of Search .................................. 600/139, 140, 600/141, 142, 143, 144, 145, 146, 147, 148, 149, 150, 151, 152, 106, 109

[56] References Cited

U.S. PATENT DOCUMENTS

| 4,329,980 | 5/1982 | Terada ...................................... 600/144 |
| 4,890,602 | 1/1990 | Hake ........................................ 600/144 |
| 4,977,877 | 12/1990 | Gouda . |
| 5,179,935 | 1/1993 | Miyaga ................................ 600/144 X |
| 5,482,029 | 1/1996 | Sekiguchi ............................ 600/146 X |

FOREIGN PATENT DOCUMENTS 3-43802  4/1991  Japan .
5-91971  4/1993  Japan .

Primary Examiner—Beverly M. Flanagan
Attorney, Agent, or Firm—Louis Weinstein

[57] ABSTRACT

A densely wound coil and a wire which passes through the coil are inserted into a flexible part which has a flexibility. The coil which is fixed in the vicinity of a distal end of the wire has a proximal end thereof which is regulated in movement toward a rearward side by a stopper. The wire which extends rearward from the proximal end of the coil has a proximal end thereof which is drawn or pulled toward the rearward side by angular movement of an adjustment knob which is provided in the vicinity of a forward end of an operation part. By this traction, a compressive force is relatively applied to the coil to make flexibility of the coil changeable. Indicia associated with the adjustment knob alerts the user to the level of flexibility to which the adjustment knob is moved.

14 Claims, 22 Drawing Sheets

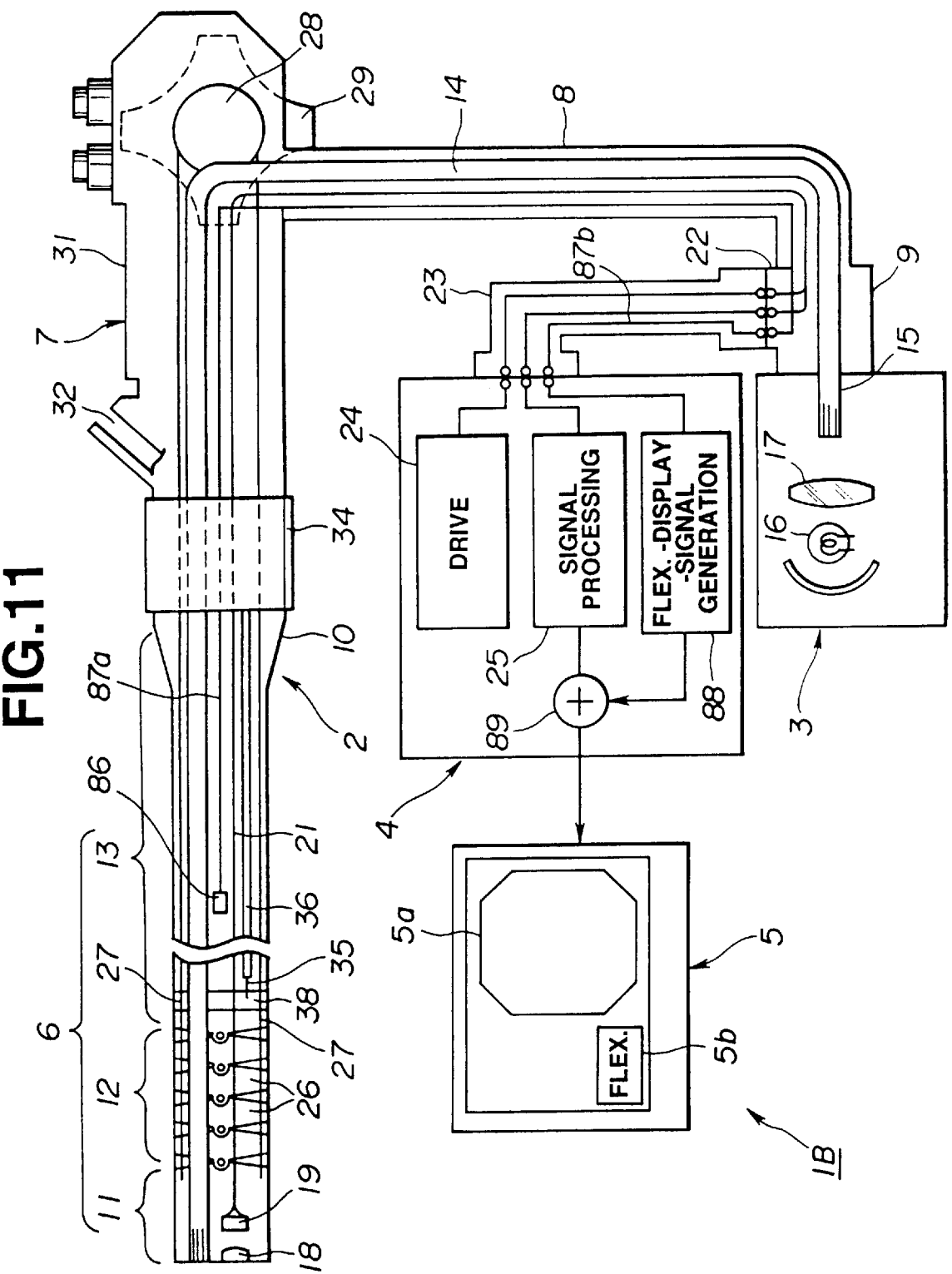

ENDOSCOPE PROVIDED WITH FUNCTION OF BEING LOCKED TO FLEXIBILITY OF INSERTION PART WHICH IS SET BY FLEXIBILITY MODIFYING OPERATION MEMBER

This application is a continuation of Ser. No. 08\712914, filed Sep. 12, 1996, now U.S. Pat. No. 5,810,715.

BACKGROUND OF THE INVENTION

1. Field of the Invention and the Description of Related Art

The present invention relates to an endoscope which is provided with a function of being locked to flexibility modifying operation member which is provided at an operation part.

In recent years, an endoscope has widely been used in which an elongated insertion part is inserted into a body cavity, to thereby observe an inspection objective part within the body cavity without the necessity of incision or excision and, under certain circumstances, to thereby use a treatment tool so as to be able to perform therapy and treatment.

The insertion part of the endoscope is so arranged as to have flexibility so as to be capable of being inserted into a bent or curved insertion path. There are cases, however, where, because of this flexibility, azimuth or direction of the forward-end side is not determined with respect to the hand side so that it becomes difficult to introduce the insertion part in the objective or a target direction.

In order to cope therewith, disclosed in U.S. Pat. No. 4,977,887, which serves as a first prior-art example, is an endoscope in which two helical tubes which are different in diameter from each other are provided in the insertion part, a rigidity controller which is provided at a grip part is operated to change a diameter of the inside helical tube whereby flexibility of the insertion part can be modified.

The prior-art example is of such a structure that a rearward end of the inside helical tube is moved spirally by operation of the rigidity controller and, thereupon, the diameter of the inside helical tube is modified as a whole. Accordingly, it is considered that it is extremely difficult to hold, to a uniform diameter, various portions of the insertion part.

Specifically, setting is made such that a striplike member which forms the inside helical tube is displaceable other than both ends thereof, and is formed spirally so that a diameter thereof is uniform. Even if a slight variation exists in characteristic thereof, however, the diameters thereof differ from each other. Further, when inserted into the body cavity, since forces which act upon a diameter of a portion thereof which is arranged within a curved curvature portion and a portion thereof which is arranged within a straight portion are different from each other, portions which are high in flexibility and portions which are low in flexibility are locally formed.

Moreover, even if adjustment or regularity is, first, made to have a uniform radius, the insertion part is inserted into the bent body cavity. Accordingly, if bending is repeated, the insertion part is apt to be deformed. Thus, it is made difficult to set the insertion part to flexibility uniform in a longitudinal direction of the insertion part, or the like. Accordingly, an endoscope is desired which can adjust the flexibility uniformly. Furthermore, this prior-art example has no lock mechanism to be described later.

For this reason, disclosed in Japanese Utility Model Unexamined Publication No. HEI 3-43802 (43802/1991) which serves as a second prior-art example is an arrangement which is provided with flexibility variable means which comprises a coil pipe and a wire, within the endoscope. According to the arrangement in this prior-art example, a compressive force can act relatively to the coil by operation to pull the wire, to modify the flexibility of the coil, an operator who performs an endoscope inspection can adjust flexibility of the insertion part by simple operation, and it is possible to facilitate insertion also into the bent path.

Since the wire which is arranged longitudinally of the insertion part is pulled to thereby compress the coil in the longitudinal direction of the insertion part, this second prior-art example can provide substantially equal compressive forces to various parts of the coil without being almost influenced upon a change in the diameter of the coil in a direction perpendicular to the compressive force. Thus, the second prior-art example can equally or uniformly adjust the flexibility longitudinally of the insertion part, by far, more than the first prior art example.

On one hand, the prior-art example requires considerably large or high capacity to pull the wire so as to have required hardness. An operation level of this prior-art example is not provided with a lock mechanism for, when the lever is operated to a certain hardness of the flexibility, holding the lever as a state of the hardness is required.

Accordingly, if a hand is removed from the lever which is operated under a hardened state, there is the possibility that the lever is naturally returned to an original position. This is useful when the insertion part is desired to be hardened instantaneously (volatility is desired to be raised). When it is desired, however, that the insertion part is inserted as the hard state is, such as the time of insertion into a depth of a large intestine, or the like, the lever must always be pressed down by the hand. Thus, operability is low.

Further, Japanese Patent Unexamined Publication No. HEI 5-91971 (91971/1993) discloses an endoscope which is provided with a flexibility modifying operation part at rearward ends of a coil and a wire which extends from an operation part.

Normally, the endoscope is of a structure in which a grip part which is provided in the vicinity of a proximal end of the operation part of the endoscope is gripped by an operator, and operation such as curvature or the like can be performed by the gripped hand. For this reason, in the above-described prior-art example, since the flexibility modifying operation part is provided at a position which extends from the operation part, the gripped hand must be removed from the operation part and be operated so that the flexibility is made variable. Thus, an arrangement which improves operability is desired.

OBJECTS AND SUMMARY OF THE INVENTION

A first object of the present invention is to provide an endoscope having improved operability in which flexibility can be adjusted uniformly in a longitudinal direction of an insertion part, the flexibility can be regulated under a state in which an operation part is gripped, and, even if a hand is left after the flexibility has been adjusted, it can be held to the flexibility state.

A second object of the present invention is to provide an endoscope in which an operator can know a set flexibility state.

According to the present invention, there is provided an endoscope which comprises:

an elongated insertion part which is provided with a flexible part having flexibility with respect to bend;

an operation part which is formed in the vicinity of a proximal end of said insertion part, and which is provided with a grip part which is gripped by an operator;

illuminating-light output means provided at a forward-end part of said insertion part, for outputting illuminating light and an objective optical system for producing an image of an object, which is illuminated by said illumination light;

a flexibility varying member which is arranged in a longitudinal direction of said flexible part and in which a compressive force acts whereby flexibility with respect to curvature varies;

a flexibility operation member which is provided at said operation part and which performs operation to vary said flexibility of said flexibility varying member; and a lock member for making said flexibility varying member lockable at a plurality of different flexibility states, correspondingly to operation of said flexibility operation member.

Thus, it is possible to adjust the flexibility uniformly in a longitudinal direction of the insertion part, and the flexibility can be adjusted under a state in which the operation part is gripped. Even if a hand is removed after the flexibility has been adjusted by the lock member, it is possible to hold the endoscope under the flexibility state.

BRIEF DESCRIPTION OF THE DRAWINGS

FIGS. 1 to 6 relate to a first embodiment of the present invention, FIG. 1 being a brief arrangement view of an endoscope apparatus which is provided with the first embodiment;

FIG. 2 is a cross-sectional view showing an arrangement of an endoscope according to the first embodiment;

FIG. 6 is a view schematically showing a manner in which a flexibility adjustment knob is operated:

FIG. 7B is a side elevational view showing a part of a state in which the flexibility adjustment knob is rotated under a state illustrated in FIG. 7A, to reduce flexibility;

FIG. 11 is a simplified view of an endoscope apparatus which is provided with a fifth embodiment of the present invention;

FIGS. 13 to 14B relate to a seventh embodiment of the present invention, FIG. 13 being a simplified view of an endoscope apparatus which is provided with the seventh embodiment;

FIG. 14B is a cross-sectional view showing an arrangement of a flexibility modification member;

FIGS. 16 to 20C relate to a ninth embodiment of the present invention, FIG. 16 being a cross-sectional view showing an internal stricture of an electronic endoscope according to the ninth embodiment;

FIG. 17 is a cross-sectional view of a flexibility adjustment mechanism portion of the endoscope;

FIG. 18 is an explanatory view of an operation portion of the flexibility adjustment mechanism of the endoscope;

FIGS. 20A to 20C are use explanatory views when the endoscope is inserted into a large intestine in an oral anus manner;

FIG. 22 is a cross-sectional view of a portion of an insertion port for the endoscope;

FIG. 23 is a perspective view of an flexibility adjustment member which is used in the endoscope;

FIG. 26 is a cross-sectional view of an operation portion of an flexibility adjustment mechanism;

FIG. 28 is a cross-sectional view of an operation portion of a flexibility adjustment mechanism;

FIGS. 29 to 32C relate to a fourteenth embodiment of the present invention, FIG. 29 being a view showing an entire or overall arrangement of an endoscope apparatus which is provided with the fourteenth embodiment;

FIG. 30 is a cross-sectional view in an axial direction, showing an internal arrangement in the vicinity of a connection part between a curvature part and a flexible part in an insertion part of an endoscope relating to the fourteenth embodiment;

FIG. 31 is an arrangement view showing an arrangement of a flexibility adjustment operation mechanism of flexibility variable means which is provided on an operation part;

FIGS. 32A to 32C are function explanatory views for describing a method of insertion when the insertion part of the endoscope is inserted into a large intestine;

DETAILED DESCRIPTION OF THE PREFERRED EMBODIMENTS

Figure 1:
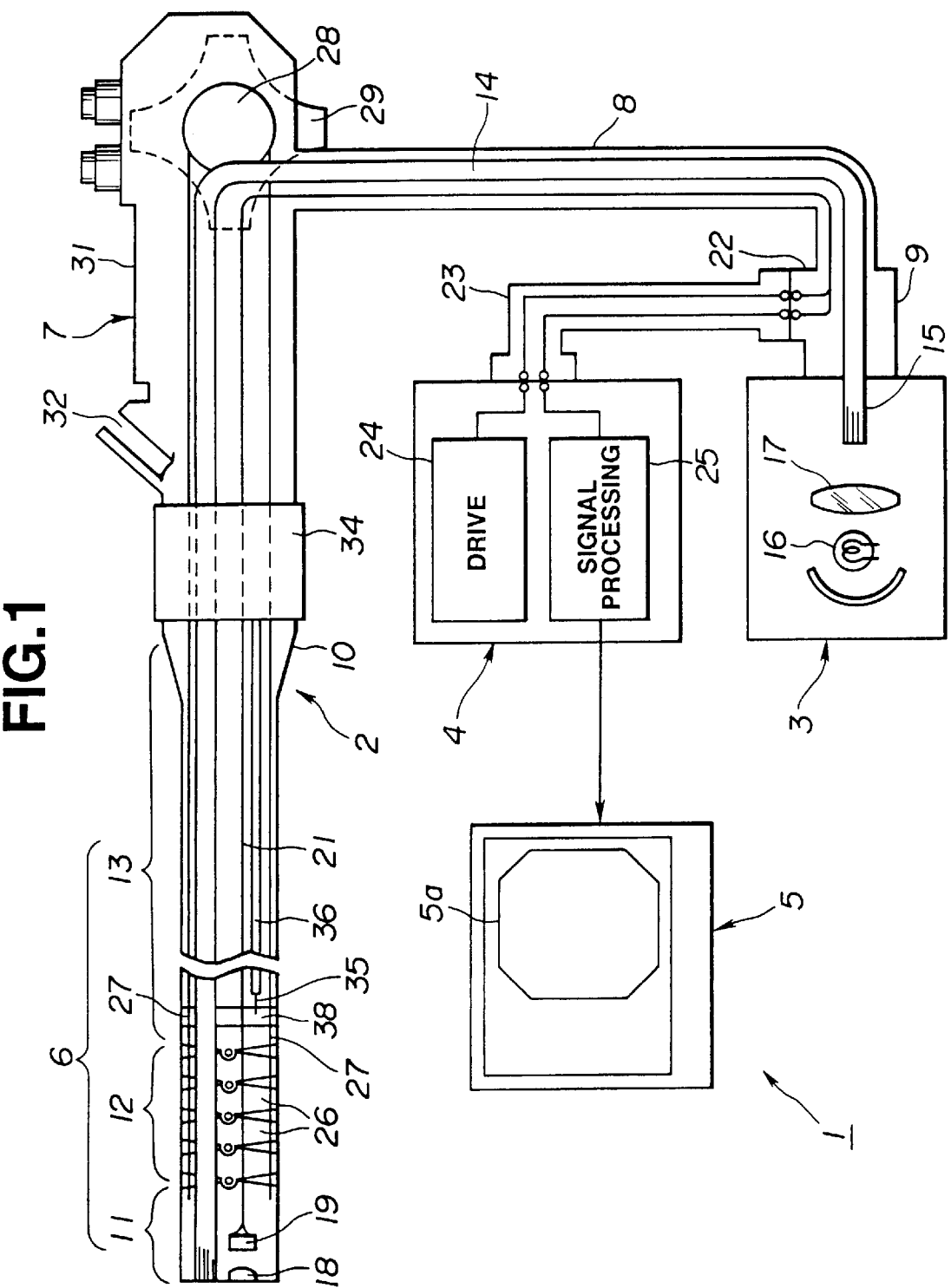

As shown in FIG. 1, an endoscope apparatus 1 comprises an electronic endoscope 2 according to a first embodiment, which has image pickup means built therein, a light source device 3 for supplying an illumination light to the electronic endoscope 2, a signal processing device 4 for processing an image pickup signal which is outputted from the electronic endoscope 2, and a color monitor 5 for displaying a video image signal which is outputted from the signal processing device 4, on an image plane.

The electronic endoscope 2 is provided with an elongate insertion part 6, an operation part 7 large in width, which is connected to the side of a rearward end of the insertion part 6, and a universal cable 8 which extends from the side part of the operation part 7. The universal cable 8 has an end thereof which is provided with a connector 9. The connector 9 can detachably be connected to the light source device 3.

The insertion part 6 comprises, from the side of a distal end thereof, a hard forward-end part 11, a curveable curvature part 12 formed at a rearward end of the forward-end part 11, and a flexible part 13 which is formed at a rearward end of the curvature part 12, which is elongated and which has flexibility with respect to bending. The flexible part 13 has the rearward end thereof which is connected to a forward end of the operation part 7. The flexible part 13 has the rearward end thereof whose outer periphery is provided with a failure prevention member 10 which has a tapered shape or form and which has a failure prevention function.

A light guide 14 which has flexibility and which consists of a fiber bundle which has a function to transmit the illumination light is inserted into and passes through the insertion part 6, the operation part 7 and the universal cable 8. A light-guide connector part 15 which is so fixed as to project into the connector 9 is connected to the light source device 3, whereby the illumination light of a lamp 16 within the light source device 3 is converged by a lens 17 so as to be supplied to an end face of the light-guide connector part 15.

The illumination light which is transmitted by the light guide 14 is outputted forwardly from a forward-end face which is fixed to an illumination window in the forward-end part 11, to illuminate an object such as an affected body part or the like. An optical image of the illuminated object is produced at an imaging position by an objective lens 18 which is mounted to an observation window which is provided in the forward-end part 11 adjacent to the illumination window. At this imaging position, a charge coupled device (abridged as CCD") 19 is arranged which serves as an image pickup element which is provided with a function to perform photoelectric conversion or transfer, to convert the optical image to an electric signal.

The CCD 19 is connected to one end of a signal cable 21. The signal cable 21 is inserted into and passes through the insertion part 6 or the like, and has a rearward end thereof which is connected to an electric connector 22 of the connector 9 and which is coimected to the signal processing device 4 through an external cable 23 which is connected to the electric connector 22. A CCD drive signal which is generated by a drive circuit 24 within the signal processing device 4 is applied to the CCD 19, whereby the photoelectrically converted image pickup signal is read out. The image pickup signal is inputted into a signal processing circuit 25 within the signal processing device 4, to perform processing to be converted to a standard video signal. The standard video signal is inputted to the color monitor 5 to display, in color, the image which is imaged to the CCD 19, in an endoscope image display region 5a.

The curvature part 12 which is provided adjacent the foiward-end part 11 is arranged such that a plurality of curvature pieces 26 in the form of a ring are connected to the adjacent curvature pieces 26 by rivets or the like at positions corresponding to the top and bottom and the right and left, angularly movably. The curvature piece 26 at the most forward end or a rearward end of curvature wires 27 which are fixed to the forward end part 11 is connected to a sprocket 28 within the operation part 7. A curvature operation knob 29 which performs curvature operation is mounted to a shaft of the sprocket 28 (In FIG. 1, for simplification, an outline or a summary of a curvature mechanism only in a top and bottom direction or a left and right direction is shown).

The arrangement is such that such operation as to angularly move the curvature operation knob 29 is performed, whereby one of the pair of curvature wires 27 which are arranged along a top and bottom direction or a left and right direction is pulled, and the other is slackened so that the curvature part 12 can be curved toward the side of the pulled curvature wires 27.

The operation part 7 is provided with a grip part 31 on the forward side more than the position at which the curvature operation knob 29 is provided. Thus, the arrangement is such that the operator can perform operation or the like of the curvature operation knob 29 by a one-side hand which grips the grip part 31 (fingers such as a thumb and the like which are not used for the gripping).

Moreover, a treatment-tool insertion port 32 is provided in the side of the forward end further forward than the grip part 31. The arrangement is such that a treatment tool is inserted from the treatment-tool insertion port 32, whereby the forward-end side of the treatment tool projects from a channel outlet in the forward-end part 11 through an interior treatment-tool channel 33 (refer to FIG. 3) so that processing such as excision of a polyp, or the like can be performed.

Furthermore, the present embodiment is arranged such that, for example, a cylindrical flexibility adjustment knob 34 which performs flexibility adjustment operation is provided at the forward end of the operation part 7 which is adjacent the failure prevention member 10, and operation to angularly move the flexibility adjustment knob 34 is performed whereby flexibility of the flexible part 13 can be modified through a flexibility modification wire (hereinafter simply abridged as "wire") 35 and a flexibility modification coil (hereinafter simply abridged as "coil") 36 which form flexibility variable means which is arranged within the flexible part 13.

The flexibility adjustment knob 34 is provided on the operation part 7, whereby the operator can operate the flexibility adjustment knob 34 in the vicinity of the grip part 31 by one hand, while the operator grips the grip part 31 by the other hand. Thus, the arrangement is one which is superior in operability.

Figure 2:
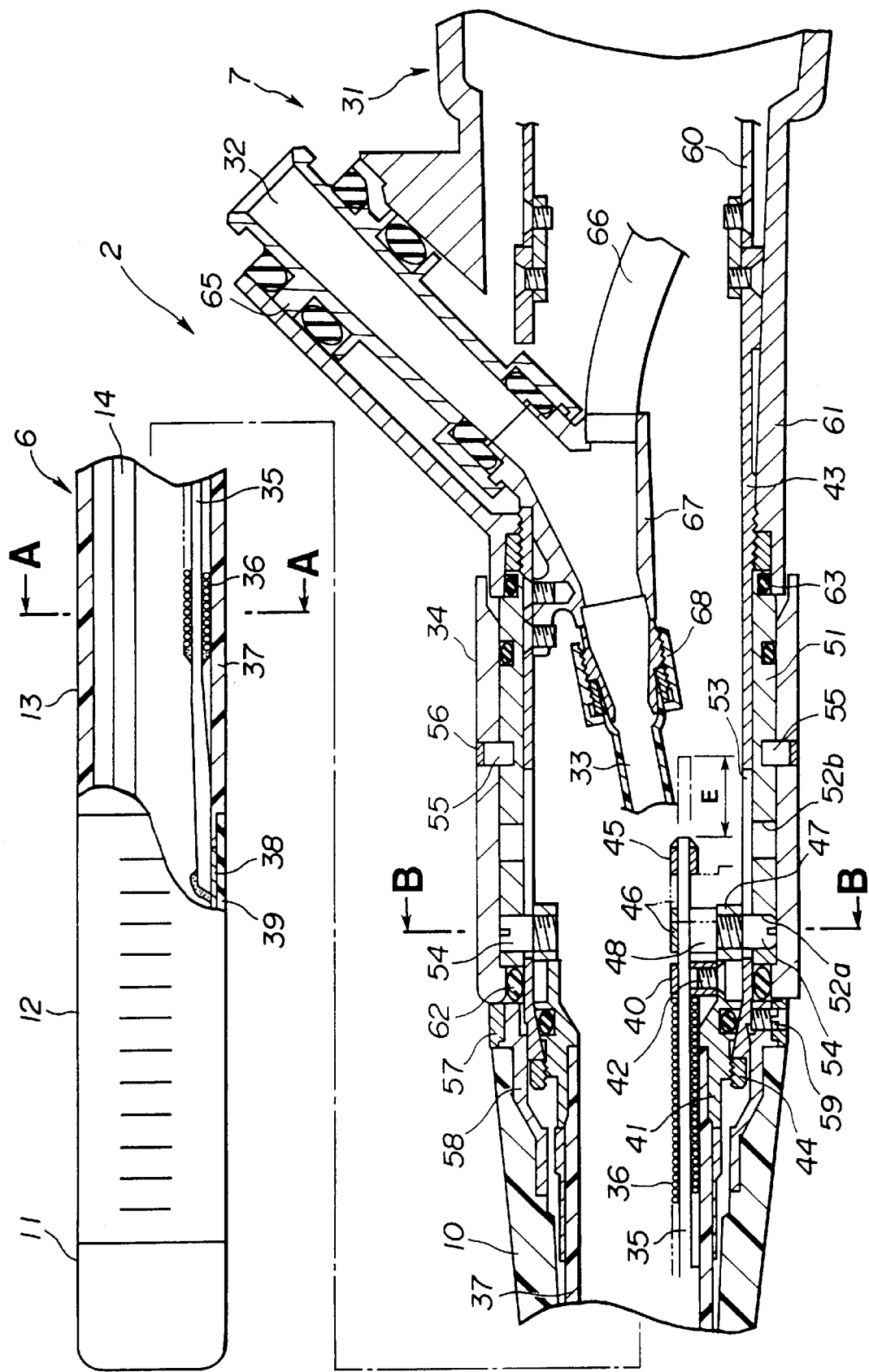

FIG. 2 shows a more concrete structure of the insertion part 6 and the operation part 7 of the electronic endoscope 2. Provided in a flexible pipe 37 which forms a skin of the flexible part 13 are the wire 35 for transmitting a force when the flexibility adjustment knob 34 is operated, and the coil 36 into and through which the wire 35 is inserted and passes and around which (the wire) is wound spirally under a state approximate to close winding.

The wire 35 has a forward end thereof which projects from the forward end of the coil 36 and which is firmly fixed by brazing or the like to a rigid connection pipe 38 which connects the curvature part 12 and the flexible part 13 to each other. The connection pipe 38 is secured to the curvature piece 26 at the most rearward end. Alternatively, the curvature piece 26 at the most rearward end may also serve the function of the connection pipe 38. The curvature pieces 26 which include the connection pipe 38 are covered with a skin 39 which has elasticity, such as a rubber tube or the like.

Further, the coil 36 has a forward end thereof which is firmly fixed to the wire 35 by brazing or the like, at a halfway position which is slightly more rearward than the forward end of the wire 35. The coil 36 has an end thereof on the side of hand, which bumps against a pulling member 46 which is arranged within a forward end of the operation part 7, so that movement rearwardly from this position is regulated (obstructed or hindered).

The wire 35 which is inserted into the interior of the coil 36 passes through a hole in a coil stopper 40 to the rearward side. The wire 35 is movable with respect to the coil 36. In this connection, the coil 36 is under a state which is almost not rotated.

The coil stopper 40 is fixed by a screw 42 to a rearward-end base 41 which fixes the rearward end of the flexible pipe 37 to the operation part 7. The rearward-end base 41 is fixed by a nut 44 at a location in the vicinity of a forward end of a cylindrical pipe 43 which is arranged at an outer periphery thereof. On one hand, a wire stopper 45 which is in the form of a ring is firmly fixed, by brazing or the like, to an end of the wire 35 at hand, that is, to a rearward end thereof.

Moreover, the traction member 46 which is movable longitudinally is arranged between the coil stopper 40 and the wire stopper 45. The traction member 46 is fixed to a moving ring 47 in such a manner that the wire 35 passes through a groove 48.

Figure 3A:
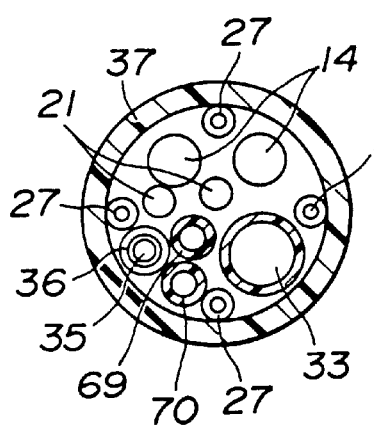
FIGS. 3A and 3B are cross-sectional views taken along lines A—A and B—B in FIG. 2, respectively.
Figure 3B:
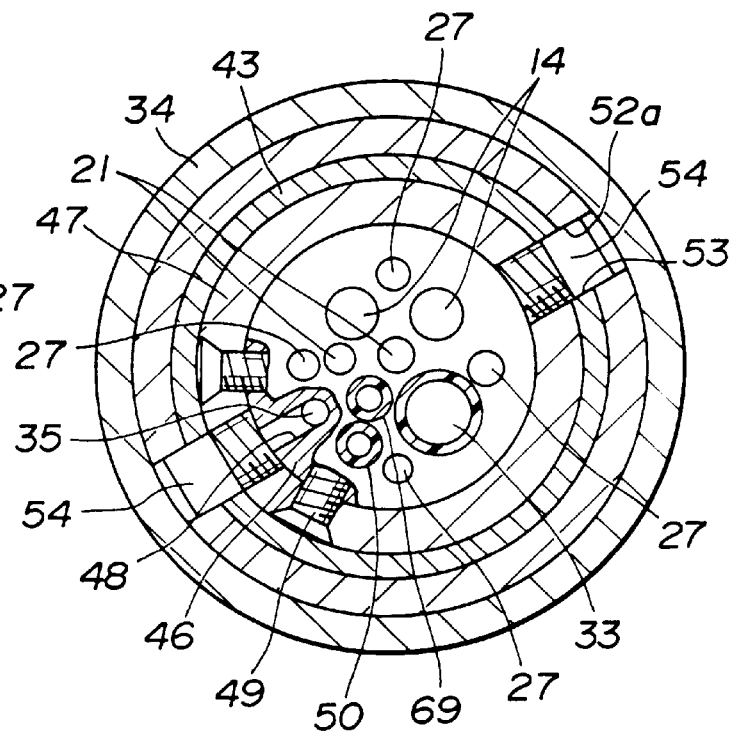

Specifically, as shown in FIG. 3B, the traction member 46 which is formed with the groove 48 through which the wire 35 passes radially is fixed to an inner peripheral surface of the toric moving ring 47 by a screw 49.

The moving ring 47 is movable axially (longitudinally) within the cylindrical pipe 43. Accordingly, when the traction member 46 is moved rearwardly together with the moving ring 47, the traction member 46 bumps against the wire stopper 45 as shown by a two-dot-and-chain line in FIG. 2. Furthermore, such operation as to move the traction member 46 rearwardly is performed whereby the wire stopper 45 is also moved rearwardly.

Under a state in which the wire stopper 45 is not moved rearwardly, the coil 36 whose movement rearwardly is regulated by the coil stopper 40 is under a state in which flexibility is the highest, that is, under a soft state the easiest to be bent.

To the contrary, when the coil stopper 40 is moved rearwardly so that the rearward end of the wire 35 is also moved rearwardly simultaneously, such a compressive force as to press the coil 36 against the forward side relatively acts on the coil stopper 40.

Specifically, a force which moves the rearward end of the wire 35 rearwardly is applied whereby the compressive force is imparted to the coil 36. The arrangement is such that, by the compressive force, it is possible to set the flexibility of the coil 36 which has flexibility, to a low state, that is, to a hard state in which it is difficult to be curved. In this case, the magnitude of the compressive force to the coil 35 can be modified in accordance with an amount of movement toward the rearward side of the coil stopper 40. Accordingly, the arrangement is such that the magnitude of the flexibility can be changed.

A cam tubular body 51 is covered on the outside of the aforesaid cylindrical pipe 43. The cam tubular body 51 is provided spirally with cam grooves 52a and 52b respectively at two opposed locations of a pipe body portion. Further, the cylindrical pipe 43 is also provided with an elongated hole 53 aligned in a longitudinal direction thereof. Two pins 54 which are moved together with the moving ring 47 are fixed to the moving ring 47 at a screw part through the cam groove 52a or 52b and the elongated hole 53 outside thereof.

The elongated hole 53 is set to such a length that a moving range of the rearward end of the wire 35 or the wire stopper 45 (reference numeral E in FIG. 2) is curved.

The flexibility adjustment knob 34 is fixed to the outside of the cam tubular body 51 by means of pins 55 at a plurality of locations in the peripheral direction. Specifically, the arrangement is such that the flexibility adjustment knob 34 is formed with a pin hole which reaches to the cam tubular body 51 on the inside thereof, and the pins 55 are fitted respectively into pin holes, and the pin holes are filled up by a filler 56.

The flexibility adjustment knob 24 has a forward end thereof which bumps against an abutment member 57 in the form of a torus sot hat movement thereof forwardly is regulated. The abutment member 57 is arrangement outside at a location in the vicinity of the forward end of the cylindrical pipe 43, and is fixed, by a screw 59, to an outer periphery of a support member 58 which supports a rearward end of the failure prevention member 10.

Furthermore, a grip part pipe body 61 has a forward end thereof whose inner peripheral surface is fitted on an outer peripheral surface of the cam tubular body 51 at the rearward-end of the failure prevention member 10.

Furthermore, a grip-part pipe body 61 has a forward end thereof whose inner peripheral surface is fitted on an outer peripheral surface of the cam tubular body 51 at the rearward-end side of the flexibility adjustment knob 34. An outer peripheral surface of a forward end of the grip-part pipe body 61 is fitted on a cut-away inner peripheral surface at the rearward end of the flexibility adjustment knob 34. Specifically, the flexibility adjustment knob 34 is in sliding contact with the outer peripheral surface of the cylindrical pipe 43 through the cam tubular body 51 under a state in which movement thereof in the longitudinal direction is regulated, and is arrangement in an angularly movable manner (around the cylindrical pipe 43).

In this manner, the flexibility adjustment knob 34 is capable of being rotatively operated, but the abutment member 57 is fixed by the screw 59 as not to be rotated.

An O-ring 62 which consists of an elastic body such as rubber or the like is arranged between the inner peripheral surface of the forward end of the flexibility adjustment knob 34 and an outer peripheral surface of the cylindrical pipe 43 which is opposed against the inside thereof The flexibility adjustment knob 34 has a forward end thereof whose imier peripheral surface is abutted and pressed against the O-ring 62. Moreover, an O-ring 63 which consists of an elastic body is received in a peripheral groove which is provided on the side of the cam tubular body 51, for example, also at a location between the outer peripheral surface of the cam tubular body 51 in the vicinity of the rearward end thereof and the inner peripheral surface of the grip-part frame body 61 which is fitted in this outer peripheral surface so that the inner peripheral surface of the grip-part frame body 61 is abutted and pressed against the O-ring 63.

Namely, the arrangement is such that water tightness is secured by the O-rings 62 and 63, and a frictional force is given to the cam tubular body 51 and the flexibility adjustment knob 34, so that, even if the hand which operates the flexibility adjustment knob 34 by the frictional force is removed, it is possible to lock (or hold) it under the state.

In this manner, the present embodiment is characterized in that, even if the flexibility adjustment knob 34 is rotatably operated so that setting is made such that the hand is removed from the flexibility adjustment knob 34 under a state in which the compressive force is given to the coil 36, it is possible to maintain (lock) the state of the flexibility adjustment knob 34, by the frictional force of the O-rings 62 and 63.

In other words, the present embodiment is of a structure in which, under a state in which the flexibility adjustment knob 34 is rotatively operated by the hand to perform operation to reduce the flexibility of the flexible part 13, even if the hand is removed from the flexibility adjustment knob 34, the flexibility adjustment knob 34 is locked to the operation state, whereby it is possible to lock the coil 36 under a flexibility state which corresponds to the operation state.

In connection with the above, in order to lock the flexibility adjustment knob 34, the O-ring which generates the frictional force may be provided at locations other than the location at which the water tightness seal is performed.

Figure 4A:
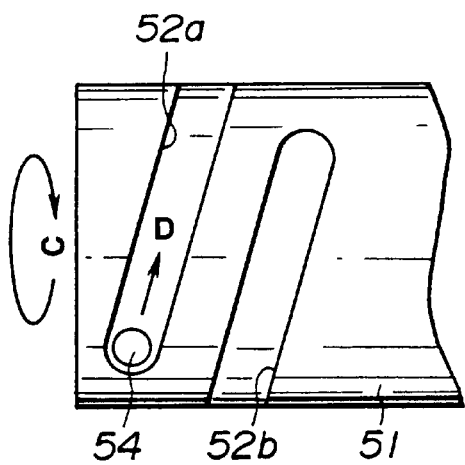
FIGS. 4A and 4B are top plan views showing an exemplification of a cam body.

FIG. 4A shows a shape or configuration of the cam grooves 52a and 52b in the cam tubular body 51. The cam grooves 52a and 52b are a double-threaded cam. One of them is shown by a cam groove 52a, while the other is shown by 52b.

The cam grooves 52a and 52b are the same in shape or form as each other, and are provided respectively at such symmetrical positions that one of them is overlapped against a position where the other is rotated 180 degrees with respect to the shaft of the cam pipe body 51. In FIG. 4A, the cam grooves 52a and 52b have a simple and smooth groove shape or form (a smooth spiral shape).

Figure 4B:
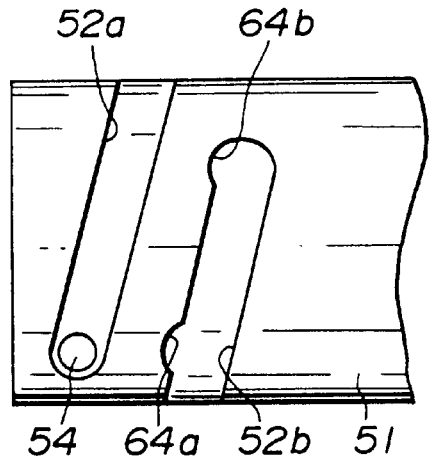

In place of the arrangement shown in FIG. 4A, the arrangement may be such that, as shown in FIG. 4B, a recess 64a exists at a location along the length of the groove 52b, or a recess 64b is provided at an end of the groove 52b, for example, so that, when pins 54 are set at these positions, a click feeling is given to the operator.

As shown in FIG. 2, an insertion-port frame body 65 which forms the treatment-tool insertion port 32 is provided at a forward position in the vicinity of the grip part 31. The insertion-port frame body 65 is connected to a branch member 67 which branches into the side of the treatment-tool insertion port 32 and the side of a suction line 66 within the interior of the operation part 7. A treatment-tool channel 33 which is provided within the insertion part 6 has a rearward end which is connected to the forward end of the branch member 67 by a connection part 68.

Further, the branch member 67 is fixed to the cylindrical pipe 43 by a screw. Moreover, the cylindrical pipe 43 has a rearward end thereof which is connected to a frame body 60 to which a curvature operation mechanism of the operation part 7, or the like, is attached, by a screw. He cylindrical pipe 43 is of such a structure that the cylindrical pipe 43 is not rotated even if the side of the flexibility adjustment knob 34 is rotated.

As shown in FIG. 3A, various visceral objects are arranged within the insertion part 6. Specifically, built therein are the four curvature wires 27 which are arranged at positions which correspond to each other in the upper and lower parts, and the left and right parts, the two signal cables 21 which are arranged in the vicinity of the center, the two light guides 14 which are arranged near the top of the center, the treatment-tool channel 33 which is arranged near the lower part, the coil 36 and the wire 35 which are arranged in the vicinity of the left part, a gas feeding tube 69 for performing gas feeding, which is arranged adjacent thereto and a water feeding tube 70 for performing water feeding.

Furthermore, visceral objects shown in FIG. 3B are arranged also within the operation part 7. The arrangement of these visceral objects is substantially similar to that in FIG. 3A.

The traction member 46 takes a certain measure of space, as shown in FIG. 3B. As shown in FIG. 2, however, the traction member 46 is located at a position more forward than the connection part 68. The traction member 46 is arranged such that, even if the traction member 46 is moved most rearwardly, the traction member 46 is located at a position further forward than the connection part 68, so that the traction member 46 can be housed or received compactly within a space which is smaller than that when it is located at a position further rearward than the connection part 68.

Figure 5A:
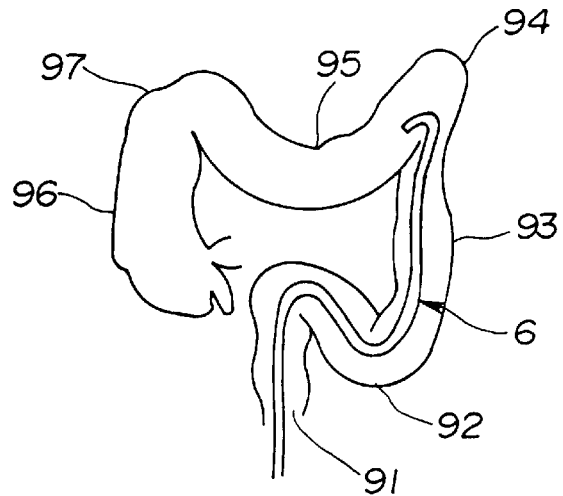
FIGS. 5A to 5C are explanatory views of function of the present embodiment.

Next, function of the present embodiment will be described with reference to a case where, as shown in FIG. 5A, the insertion part 6 of the endoscope 2 is inserted from an anus 91 toward the side of the caecum through the large intestine, to perform the endoscope inspection.

As shown by the solid line in FIG. 2, under a state in which the traction member 46 does not bump against the wire stopper 45, since no tensile force is applied to the wire 35, the coil 36 is also soft or elastic. Accordingly, the flexible part 13 is under a soft or elastic state of being apt to be bent.

As shown in FIG. 5A, the flexible part 13 is inserted into a bent, S-shaped colon 92 from the anus 91 while urging the insertion part 6 under such soft state.

Figure 5B:
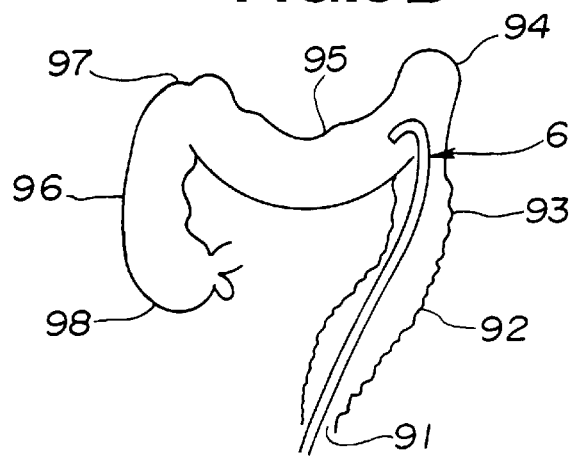

Since the flexible part 13 is under the soft state, even if it is in the bent S-shaped colon 92, it is possible to insert the flexible part 13 under a state in which a pain given to a patient is small. As shown is FIG. 5A, if the forward end of the insertion part 6 of the electronic endoscope reaches a location in the vicinity of a specific curvature 94 through a lower-line colon 93, operation to pull the insertion part 6 is performed. Then, as shown in FIG. 5B, the S-shaped colon 92 is shortened substantially into a straight line. The insertion part 6 of the electronic endoscope becomes substantially straight.

Under this state, the flexibility adjustment knob 34 is rotated in a direction which is indicated by a mark C in FIG. 4A (In FIG. 4A, it is shown under a state in which the left side is made to the side of the insertion part).

Since the flexibility adjustment knob 34 is provided in the vicinity of the grip part 31 of the operation part 7, this operation can easily be performed without removing the hand from the grip part 31, while the hand grips it.

When the flexibility adjustment knob 34 is rotated, the pin 54 is moved in the cam groove 52a (with respect to the cam tubular body 51) as shown by the solid line in FIG. 4A, as shown by an arrow D.

Further, since the pin 54 passes through an elongated hole 53 which is formed longitudinally of the cylindrical pipe 43, the moving ring 47 is moved rearwardly along the elongated hole 53, together with the pin 54. That is, actually, the pin 54 is moved in a horizontal direction (the right side) in FIG. 4A.

By this movement, the traction member 46 which is fixed to the moving ring 4 is also moved rearwardly. By this movement, when the traction member 46 is moved from a solid-line position in FIG. 2 to a position indicated by a two-dot-and-chain line, the traction member 46 bumps against the wire stopper 45.

The flexibility adjustment knob 34 is further rotated, and the traction member 46 is moved rearwardly, whereby a tensile force acts on the wire 35, and a compressive force is given to the coil 36. Thus, the coil 36 is hardened (i.e. "stiffened"). By this fact, it is possible to harden the flexible part 13.

At this time, the cam grooves 52a and 52b have smooth and simple shape or configuration. By the frictional force due to the O-rings 62 and 63 and the frictional force due to the fact that the forward end of the flexibility adjustment knob 34 bumps against the abutment member 57, however, even if the hand which operates the flexibility adjustment knob 34 is removed, it is possible to stop the pin 54 at an optional position within a moving range between a position of the forward ends of the cam grooves 52a and 52b to the rearward ends thereof. Specifically, even if the operator removes his or her hand from the flexibility adjustment knob 34, it is possible to lock (hold) the flexibility adjustment knob 34 so as not to be moved as it is.

In case of the cam groove 52a and 52b which have a smooth spiral shape as in FIG. 4A, there is the possibility that the flexibility adjustment knob 34 cannot be stopped at a location in the vicinity of a state in which flexibility is the smallest, depending upon the manner of setting of the capacity which pulls the wire 35. In this case, as shown in FIG. 4B, if the recess 64a is provided along the groove, or if the recess 64b is provided at the rearward end, it is possible to ensure that the pin 54 is stopped at the location where there is the recess 64a or 64b (Of course, the flexibility adjustment knob 34 is locked to a state corresponding to the pin 54 which is latched to the recesses 64a and 64b).

At this time, there is a click feeling if the pin 54 is put into one of the recesses 64a and 64b. By the fact that there is the click feeling, it is possible to notify the operator of the fact that it has a predetermined hardness. Accordingly, when the flexibility adjustment knob 34 is operated, it is possible for the operator to correctly grip the level of flexibility by this click feeling.

Figure 5C:
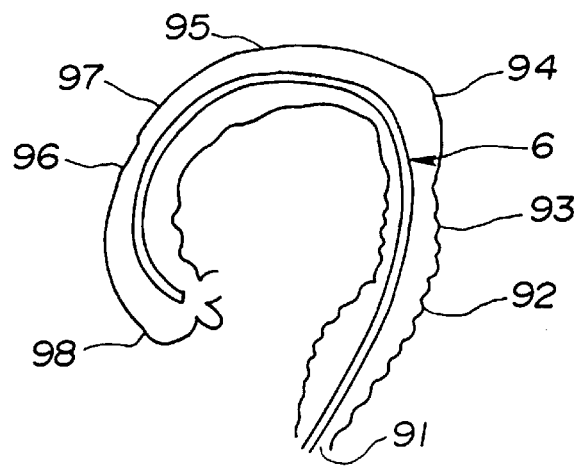

It is important when the insertion operation as shown in FIGS. 5A and 5B is performed to correctly grip the state of flexibility of the insertion part 6. In this manner, the insertion part 6 is hardened at the time of FIG. 5B and, further, the insertion part 6 of the endoscope is inserted into a traverse colon 95, a liver curvature 97, and upper-line colon 96 and a caecum 98 while urging the insertion part 6. Thus, as shown in FIG. 5C, it is possible to have the forward end of the insertion part 6 of the electronic endoscope reach the caecum 98.

At this time, since the flexible part 13 is hardened, there is less chance that the flexible part 13 is deflected small on the way. It is possible to insert the flexible part 13 quickly and easily to the caecum 98, while describing a gentle curve as shown in FIG. 5C. In this connection, if the capacity which pulls the wire 35 is the maximum 15 kg in order to bring it to the required hardness, it means a resistant force equal to or more than 15 kg (with respect to the end of the wire 35) to hold the same. Setting should be made such that the frictional force due to the O-rings 62 and 63 becomes also larger or higher than this value.

At a location having the connection part 68 and the branch member 67, the inside space of the cylindrical pipe 43 is narrowed. Further, also at a location more rearward than that, the space within the operation part 7 is narrowed because there is a mechanism for curvature operation or function. Since, however, the traction member 46 is arranged more forward than the connection part 68, it is not necessary to further thicken it with respect to the cylindrical pipe of the existing endoscope. Thus, it is possible to arrange a flexibility adjustment and operation mechanism.

In this manner, in the present embodiment, it is possible to prevent the operation part 7 from being thickened unnecessarily. Moreover, an external structure of the operation part 7 can also be realized in such a manner that, since a location having the treatment-tool insertion port 32, or the grip part 31 is originally thick in diameter, the flexibility adjustment knob 34 is arranged at a location further toward the insertion part 6 than the treatment-tool insertion port 32 whereby a portion of the flexibility adjustment knob 34 is not thickened in diameter more than the necessity.

Figure 6:
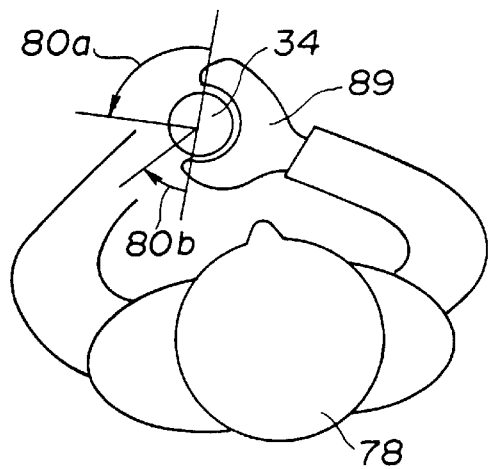

FIG. 6 shows schematically a manner when the flexibility adjustment knob 34 is provisionally seen from the rearward side of the operation part 7. A work range of a right hand 79 of an operator 78 who rotatively operates the flexibility adjustment knob 34 under a state of being gripped is, however, such that it is possible to normally rotate a work range 80a of rotation on the side of an anti-clockwise rotational direction (abridged simply as being "left rotation"), more than rotation on the side of clockwise rotational direction (the right rotation).

As has been described with reference to FIGS. 5A to 5C, since, when the insertion part 6 of the electronic endoscope is inserted into the large intestine, it is under the insertion operation when the insertion part 6 is hardened on the way from the original state in which the insertion part 6 is soft, if setting is made such that it is hardened when it is rotated in the side of the left rotation as shown in FIG. 6 in order to perform rapid or quick operation, it is possible to rapidly harden the flexibility adjustment knob 26 without, as far as, being changed in having, such as to make the state to a state in which it is the most hardened by once operation, or the like.

Then, the state is brought to a state as shown in FIG. 5C. After the insertion has been completed, since it has time to spare, even if the flexibility adjustment knob 34 is returned to a soft state while being often changed in having, by less strokes like the right rotational rotation in FIG. 6, there is no so-much bad influence upon the operator 78. In view of this, it is desirable for operating the same hardly that the flexibility adjustment knob 34 is rotated in the side of the left rotation when viewed from the rearward thereof.

The present embodiment has the following advantages:

The flexibility adjustment knob 34 is provided on the operation part 7, whereby it is possible to easily perform operation part 7, whereby it is possible to easily perform operation to modify the flexibility of the insertion part 6. Since the mechanism for locking the flexibility adjustment knob 34 which is set optionally is provided, when the operator hardens the insertion part 6, it is not necessary that the flexibility adjustment knob 34 is so gripped and restrained as not to be moved. Accordingly, the operability of the insertion operation is improved or becomes good.

Furthermore, since the traction member 46 is arranged forwardly more than the connection part 68, it is possible to arrange the flexibility adjustment mechanism such as the traction member 46 or the like without the fact that the operation part 7 is thickened more than the existing one. Thus, it is possible to keep or maintain operability and handling ability of the operation part 7 almost similar to that of the existing one.

Further, if the recesses 64a and 64b as shown in FIG. 4B are provided, it is possible that the operator grips the level of the predetermined flexibility, in a manner of the touch, by the hand which operates the flexibility adjustment knob 34.

Next, a second embodiment of the present invention will be described. An electronic endoscope 71 according to the second embodiment has an internal structure which is the same as that of the electronic endoscope 2 in FIG. 2.

Figure 7A:
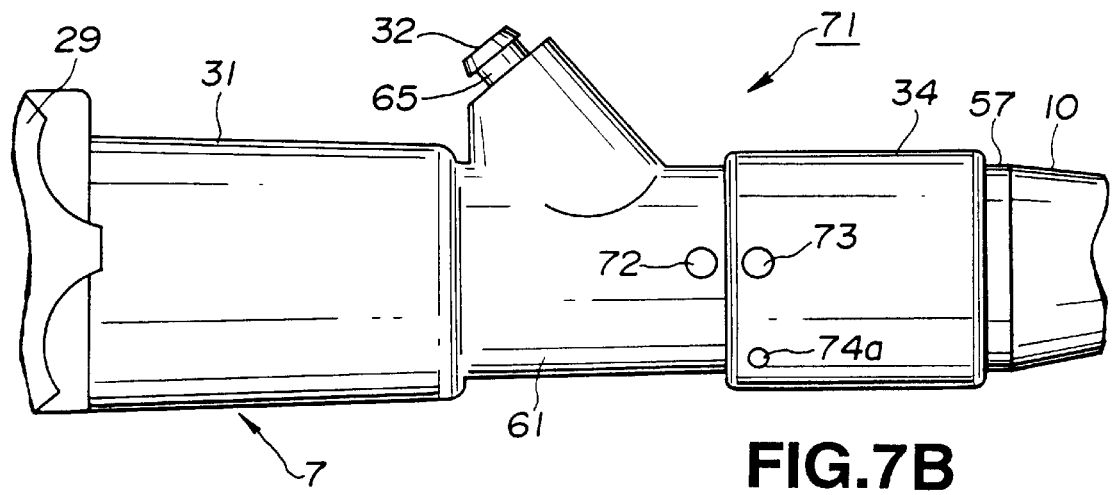
FIGS. 7A and 7B relate to a second embodiment of the present invention, FIG. 7A being a side elevational view showing an operation part of an electronic endoscope as viewed from a direction in which a curvature operation knob of the operation part is provided in projection.

As shown in FIG. 7A, an index 72 is provided in the outer surface of the operation part 7 in the vicinity of the flexibility adjustment knob 34.

A position of this index 72 is such a predetermined position that, when it is viewed from such a direction that the curvature operation knob 29 projects, the index 72 is seen at a central position on the outer surface of the operation part 7. Further accurately, the index 72 is provided at a position which can be viewed from the direction of the rotational shaft, like a position at which the rotational shaft is moved in parallel forwardly more than the grip part 31, as viewed from the direction of the rotational axis of the curvature operation knob 29.

Figure 7B:
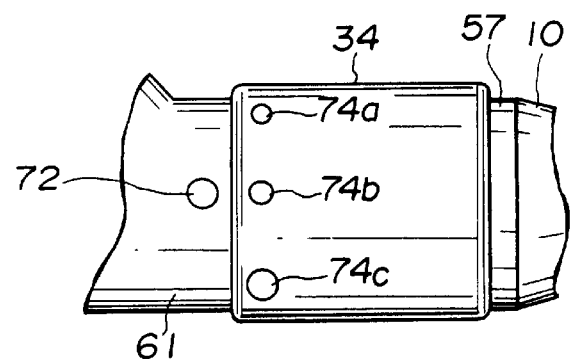

On one hand, as shown in FIG. 7B, a soft-state graduation 73, and flexibility state graduations 74a, 74b and 74c which indicate, respectively, three flexibility values are provided on the side of the rearward end of the flexibility adjustment knob 34. The index 72 and the soft-state graduation 73 have respective shapes thereof which resemble each other, or have respective colors which resemble each other.

For example, if the index 72 is circular in shape as shown in FIG. 7A, the soft-state graduation 73 is also circular. If the index 72 is rectangular in shape, the soft-state graduation 73 is also rectangular. The hard state graduations 74a, 74b and 74c are, however, different in size, shape or color from the soft-state graduation 73. By doing so, it is made clear that the soft state and the hard state are different from each other. Thus, it is made definite that the soft state is, to the last, a standard state, and the hard state is used as occasion demands.

In FIGS. 7A and 7B, not only the soft-state graduation 73, but also the hard state graduations 74a, 74b and 74c are similarly circular in shape. Thus, color is changed in such a manner that, for example, if the index 72 and the soft-state graduation 73 are white in color, the hard state graduations 74a, 74b and 74c are red in color. Moreover, also in the three hard states, the hard state graduations 74a, 74b and 74c are different in size from each other. The operator can clearly or definitely know that the hard state graduation 74b becomes larger in size than the hard state graduation 74a, and the hard state graduation 74c becomes larger in size than the hard state graduation 74b whereby it is clearly know by the operator that it is in a state which becomes more hard.

Such index 72, soft-state graduation 73 and hard state graduations 74a, 74b and 74c may be fluorescent color so as to be seen also in, for example, a dark location.

Next, operation of the present embodiment will be described.

It will easily be seen that, as shown in FIG. 7A, when the index 72 indicates the soft-state graduation 73, the insertion part 6 becomes a soft standard state. Furthermore, by the fact that the hard state graduations 74a, 74b and 74c are provided with the flexibility adjustment knob 34 is rotatively operated, it is easy to determine the degree of the flexibility level. Further, since means for notifying the flexibility level is located in the vicinity of the insertion part 6, when the insertion operation is performed, it is possible for the operator to easily determine the flexibility level of the insertion part 6.

Normally, in the video scope or the electronic endoscope, there are many cases where the grip part 31 is gripped so that the projecting direction of the curvature operation knob 29 is oriented toward a face or a thorax of the operator. Accordingly, it is desired that the index 72 is located at a position which can be viewed from a projecting direction of the curvature operation knob 29, as is in the present embodiment.

Moreover, the flexibility level is graduated on the side of the rotating flexibility adjustment knob 34, and the index 72 is provided at the immovable predetermined position, whereby the operator can determine the flexibility level if the operator sees the predetermined position without the fact that the operator always moves the operation part 7, to relaxes his or her posture.

Accordingly, according to the present embodiment, the operator can determine the level of flexibility of the insertion part 6 in a manner of visual sense. The other has advantages similar to those of the first embodiment.

Figure 8:
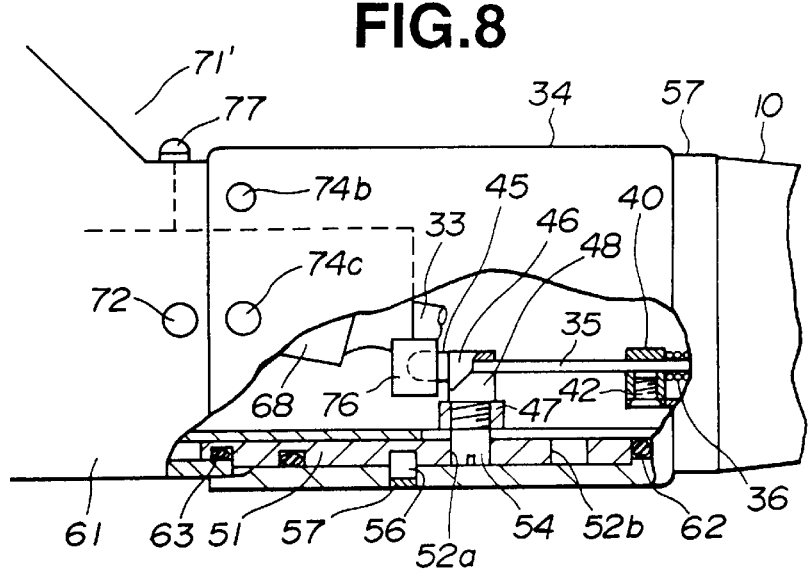
FIG. 8 is a side elevational view, partially cut away, of a structure in the vicinity of a flexibility adjustment knob of an electronic endoscope according to a modification of a second embodiment.

FIG. 8 shows a structure in the vicinity of the flexibility adjustment knob 34 of an electronic endoscope 71' according to a modification of the second embodiment. This modification is arranged such that, when set to a predetermined flexibility state, a light emitting diode (LED) 77 emits light to notify the operator in a manner of visual sense.

As shown in FIG. 8, a photo interrupter 76 is arranged such that the LED and a light receiving element are arranged respectively on opposite sides of a position where the wire stopper 45 which is impinged against the traction member 46 is moved most rearwardly, by the operation of the flexibility adjustment knob 34 and a structure is such that the LED 77 which is provided on an outer peripheral surface of, for example, the operation part 7 is driven by an output from a light receiving element of the photo interrupter 76.

In connection with the above, the wire 35 shown by the solid line in FIG. 8 corresponds to the state shown by the two-dot-and-chain line in FIG. 2. The other arrangement is similar to that of the second embodiment.

Operation of FIG. 8 will be described. As has been described in FIGS. 7A and 7B, if the flexibility adjustment knob 34 is rotated, and setting is made to a location where, for example, the index 72 indicates the hard state graduation 74c which is the smallest in flexibility, the wire stopper 45 enters within a detection space at which the LED of the photo interrupter 76 and the light receiving element are opposed to each other, so that the state is made to a state in which a light of the LED is shielded.

Then, the output level of the light receiving element which is arranged opposed thereto is changed, for example, from an L to an H. It is detected that it is set to the hardest hard state graduation 74c. Thus, the LED 77 is emitted in light. In this connection, a power source for driving the photo interrupter 76 or the like is supplied by a power-source line of a signal line which is connected to the light source device 3 or the signal processing device 4 in FIG. 1.

When it is set to the state which is the smallest in flexibility, the state is detected, and a light is emitted by the LED 77, whereby it is possible to ensure that it is locked to the value the smallest in flexibility.

Specifically, since the flexibility adjustment knob 34 which serves as the flexibility modifying operation member is such that the largest hardened state which can be operated thereby is normally set as a level required thereby, it is notified to the operator that setting is made to a location in the vicinity of the level, whereby it is possible to ensure that it is confirmed that setting is made to the state, and it is possible to know that it is locked.

In FIG. 8, description is made by the structure which detects that it is set to the hardest state. It may, however, detect the other flexibility state. Moreover, a lamp may be used to emit light in place of the LED 77.

In this manner, if the arrangement is such that the LED 77 is turned ON, the operator can definitely confirm or identify that it is set to a predetermined hardness level even at a dark location.

In this manner, it is desirable that the means for notifying the level of the hardness in a manner of visual sense is located adjacent the side of the insertion part as far as possible. At least, it is desirable that the means for notifying the level of the hardness in a manner of visual sense is located nearer to the side of the insertion part 6 than the grip part 31.

This is the reason that this is easy to know by the operator if the level of the hardness is, at last, the level of the hardness of the flexible part 13 (function of the flexible part) which is located adjacent the operation part 7, and there is means for notifying the level at a location close to the flexible part 13. Normally, in the endoscope, the grip part 31 is gripped by the left hand, and the flexible part 13 is gripped by the right hand, to operate the endoscope. In view of this, if there is means for indicating the hardness level of the flexible part 13 more forward than the grip part 31, it is easy to grip it as one on the side of the insertion part 6.

Figure 9:
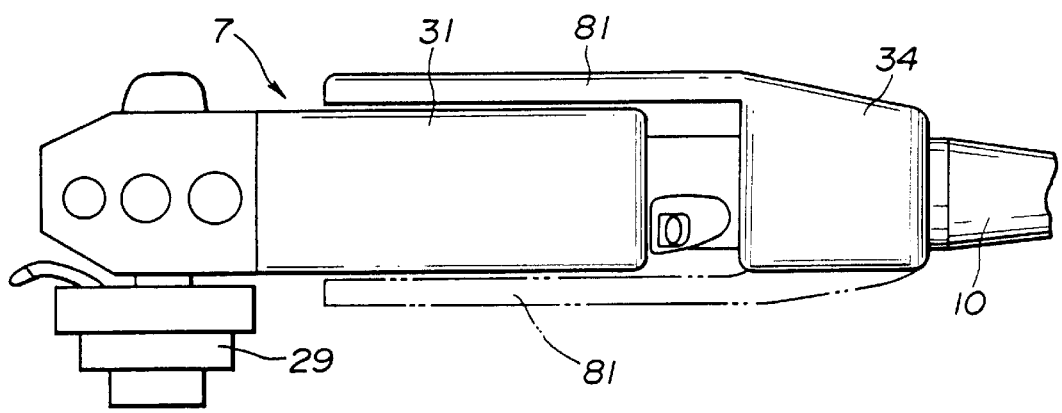
FIG. 9 is a side elevational view showing the vicinity of an operation part of an electronic endoscope according to a third embodiment of the present invention.

As shown in FIG. 9, in the present embodiment, an extension part 81, for example, is provided at the rearward end of the flexible adjustment knob 34 in the first embodiment, and the flexible adjustment knob 34 extends toward the side of the rearward grip part 31 by this extension 81. The extension 81 does not extend around the full periphery of the flexible adjustment knob 34, but is provided only at a part thereof The extension 81 is so provided as to substantially overlap or lie against the surface of the grip part 31. The other has an arrangement similar to that of the first embodiment.

Next, function of the present embodiment will be described.

If the grip part 31 of the operation part 7 shown in FIG. 9 is gripped, it is gripped together with the extension part 81. For example, it is assumed that the state shown by the solid line in FIG. 9 is the state in which the insertion part 6 is soft. At this time, the extension 81 is located on the side of the palm of a hand. Then, if the flexibility adjustment knob 34 is rotatively operated so as to be hardened, the extension 81 is moved to a position as shown by the two-dot-and-chain line, for example.

Then, since it comes up to the side opposite to the side of the palm of the hand, a grip feeling of the grip part 31 is entirely different. By this fact, the operator can correctly grip the level of hardness of the insertion part 6 by the grip feeling of the grip part 31. Further, also other than such method, the arrangement may be such that, if, for example, the flexibility adjustment knob 34 is rotated, a part of the operation part 7 is vibrated or oscillated.

If the part of the operation part is oscillated, the oscillation is transmitted to the hand which grips the same. Accordingly, also in this case, grip feelings are different from each other under a state in which the insertion part is soft and under a state in which the insertion part is hard. The operator can acknowledge a certain level of hardness by the same.

The present embodiment has the following advantages.

It is possible to determine the level of the flexibility of the operation part 7, depending upon the sense of the hand by which the operator grips the operation part 7. Even if the index 72 of the operation part 7 is not seen during the insertion operation, as the second embodiment, it is possible to determine the level of the flexibility.

Figure 10A:
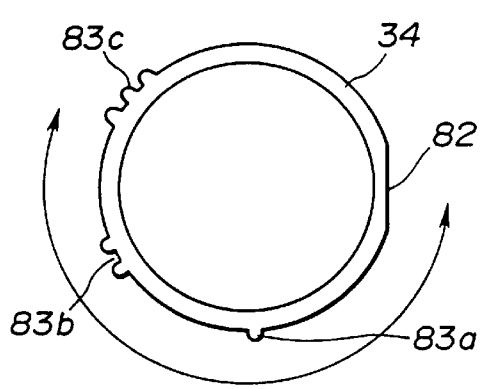
FIG. 10A is a front elevational view showing a flexibility adjustment knob in a fourth embodiment of the present invention.

FIG. 10A shows the flexibility adjustment knob 34 in a fourth embodiment. In FIG. 10A, a planar part 82 is provided on a part of the flexibility adjustment knob 34. The planar part 82 corresponds to the soft-state graduation 73 in the second embodiment. Further, the flexibility adjustment knob 34 has an outer peripheral surface thereof which is provided with small projections 83a, 83b and 83c which are different in the number of projections from each other, at positions which correspond to the flexibility levels which are different from each other. These correspond respectively to the hard state graduations 74a, 74b and 74c in the second embodiment.

Specifically, in this manner, the form or shape of the outer surface of the flexibility adjustment knob 34 is so arranged as to indicate the level of the flexibility. Further, the planar part 82 and the small projection parts 83a, 83b and 83c serve also as function of a nonskid part so that it is possible to perform operation without slippage when the flexibility adjustment knob 34 is rotatively operated.

Figure 10B:
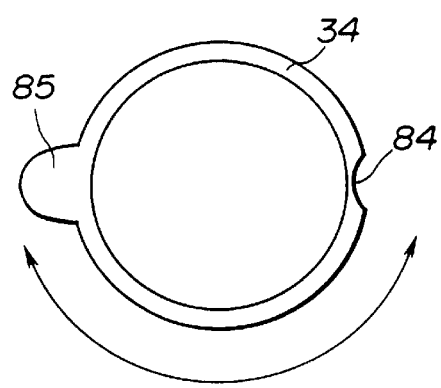
FIG. 10B is a front clevational view showing a flexibility adjustment knob in a modification of the fourth embodiment.

A modification in FIG. 10B is so arranged that a recess 84 is provided at a portion which corresponds to the soft-state graduation 73 in the second embodiment, and a projection 85 is provided at a portion which corresponds to the hard state graduation 74c in the second embodiment. In this manner, small unevenesses are eliminated, and the unevenesses are made to a relatively large unevenness as the recess 84 and the projection 85, whereby cleaning ability is made superior.

Next, function and effects (advantages) of the present embodiment will be described.

The operator can considerably correctly grip in what rotational state the flexibility adjustment knob 34 is set merely by gripping the flexibility adjustment knob 34 without specially seeing it, i.e., in what manner the level of the flexibility of the flexible part 13 is, when the flexibility adjustment knob 34 is rotatively operated. Moreover, the unevenness on the outer surface of the flexibility adjustment knob 34 serves also as a non-slip.

FIG. 11 shows an endoscope apparatus 1B which is provided with a fifth embodiment according to the present invention. The present embodiment is arranged such that the magnitude of the flexibility is detected, and the detected magnitude of the flexibility is displayed on a monitor.

For example, a flexibility detection sensor 86 which comprises a distortion sensor for detecting flexibility of the flexible part 13, or the like, is so provided as to be fixed to the inner wall of the flexible pipe 37, at a suitable position such as a center, or the like, of the flexible part 13 of the electronic endoscope 2, in the longitudinal direction. The flexibility detection sensor 86 is arranged such that an amount of distortion varies in accordance with the tensile force which acts in the longitudinal direction of the flexible pipe 37, to detect the flexibility from the amount of distortion.

A distortion signal which is detected by the flexibility detection sensor 86, or a flexibility detection signal is inputted to a flexibility-display-signal generation circuit 88 which is provided within the signal processing device 4, through a signal line 87a which is inserted into and passes through the flexible part 13, the operation part 7 and the universal cable 8, and further, a signal line 87b within the scope cable 23.

The flexibility-display-signal generation circuit 88 comprises a character generation circuit, or the like, for displaying a value of the flexibility which is detected from a flexibility detection signal which is detected by the flexibility detection sensor 86, as, for example, numerical values. Specifically, the flexibility-display-signal generation circuit 88 performs conversion from the flexibility detection signal to the flexibility display character signal.

The flexibility display character signal which is outputted from the flexibility-display-signal generation circuit 88 is inputted to a mixer 89, and is superimposed upon a video signal which is outputted from the signal processing circuit 25 so as to be outputted to the color monitor 5, to thereby display the flexibility which is detected to a flexibility display region 5b in the display surface of the color monitor 5.

The other arrangement is similar to that of the first embodiment.

Generally, in case of the electronic endoscope 2, the insertion operation or the like is executed, while the endoscope image which is displayed on the color monitor 5 is watched. Accordingly, if the flexibility of the flexible part 13 is simultaneously displayed on the display surface of the color monitor 5 as the present embodiment, it is possible to confirm the magnitude of the flexibility without the fact that a line of sight is transferred toward the flexibility adjustment knob 34, in order to confirm the graduation position, as the second embodiment.

Figure 12:
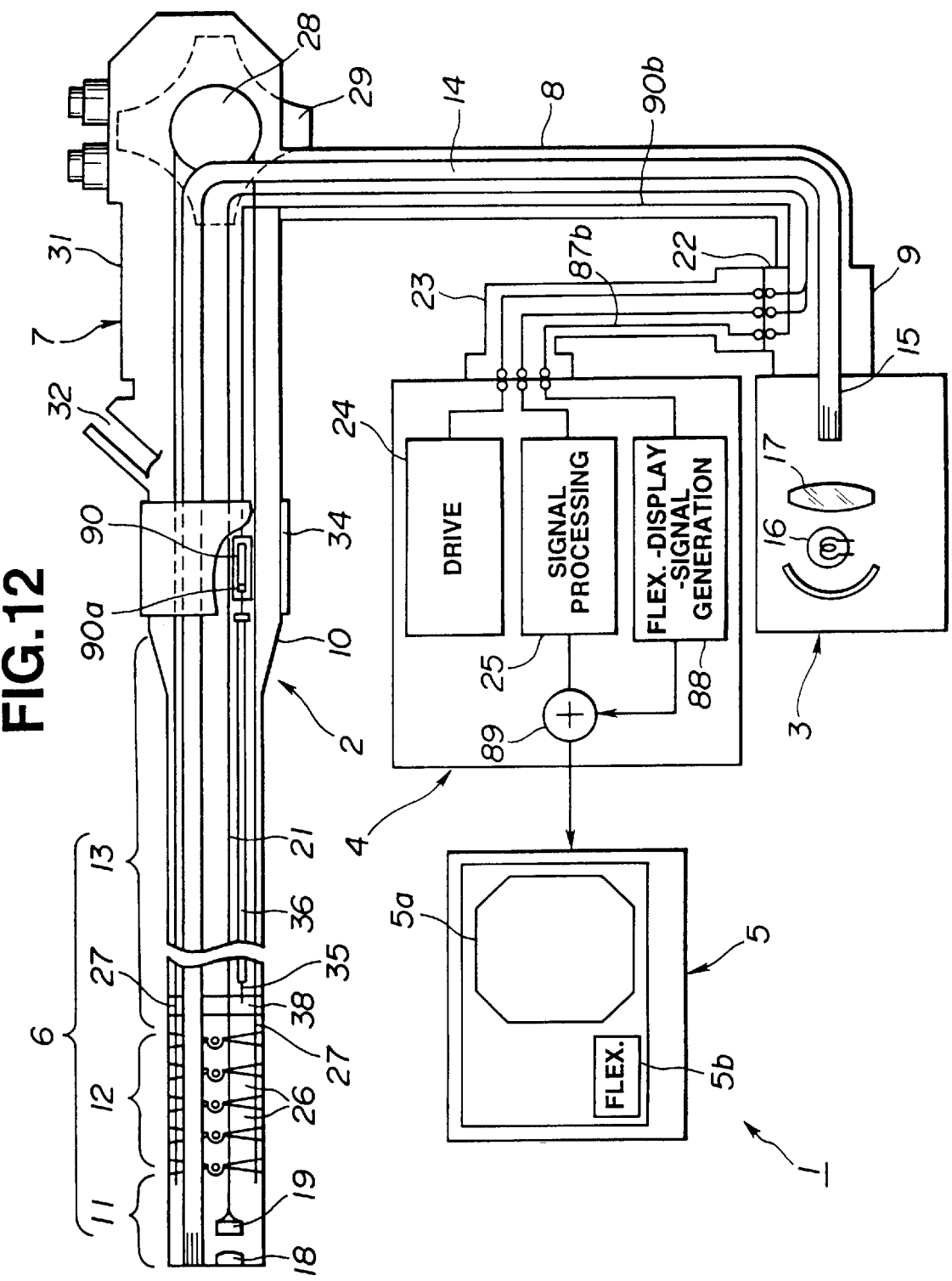
FIG. 12 is a simplified view of an endoscope apparatus which is provided with a sixth embodiment of the present invention.

FIG. 12 shows an endoscope apparatus 1C which is provided with the electronic endoscope 2, according to a sixth embodiment of the present invention. The present embodiment is so arranged that means for detecting an amount of wire traction is provided within the operation part 7, and a corresponding magnitude of the flexibility is displayed on the color monitor from the detected amount of traction.

In the endoscope apparatus 1C in FIG. 12, the arrangement is as follows. That is, if a slide lever 90a which is connected to a resistance variable terminal of a slide-type variable resister 90 is secured to a rearward end of the wire 35, as shown in FIG. 12, in place of the fact that the flexibility detection sensor 86 in FIG. 11 is provided, and if the flexibility adjustment knob 34 is angularly moved to move the rearward end of the wire 35 rearwardly, the slide lever 90a which is secured to the rearward end thereof is also moved rearwardly, and resistant values between the resistance variable terminal and one end thereof vary together with movement of the slide lever 90a.

The resistant values are inputted to the flexibility-display-signal generation circuit 88 within the signal processing device 4, through a signal line 90b which is connected to the slide-type variable resistor 90, or the like. A character of a corresponding value of the flexibility is read out from the resistant value, is superimposed upon the video signal through the mixer 89, and is displayed on the flexibility display region 5b of the color monitor 5.

The present embodiment has function and advantages substantially similar to those of the fifth embodiment.

In connection with the above, in the present embodiment, the corresponding flexibility is displayed by the numerical values in accordance with the amount of traction of the wire 35. The flexibility, however, may be displayed in the form of a bar graph. Furthermore, it may be notified by voice in accordance with a predetermined amount of traction. Further, when notified, it may be outputted from the electronic endoscope or a peripheral device.

Figure 13:
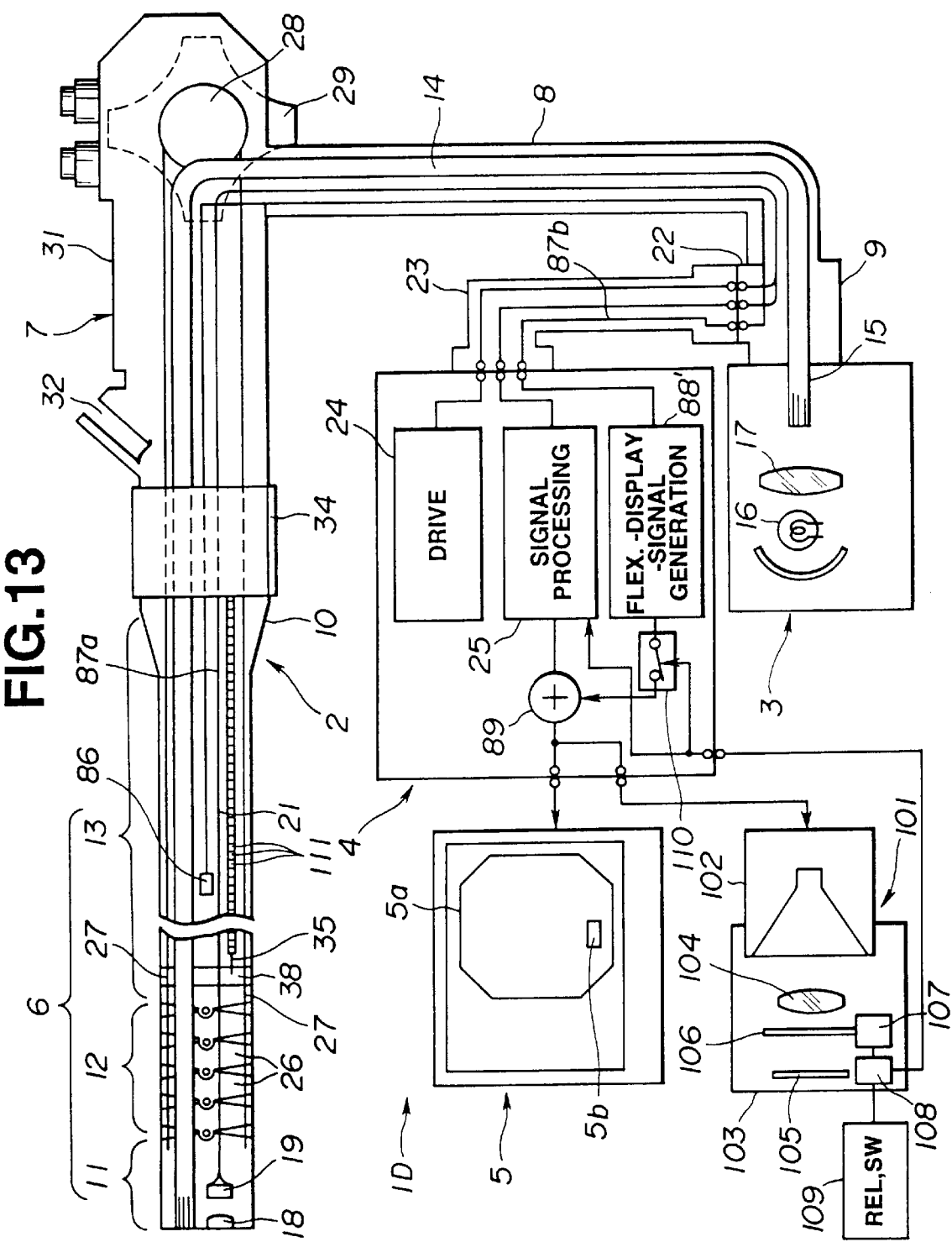

FIG. 13 shows an endoscope apparatus 1D which is provided with the electronic endoscope 2 according to a seventh embodiment of the present invention. The present embodiment further comprises a monitor photographing device 101, in the endoscope apparatus 1B in FIG. 11. The monitor photographing device 101 comprises a color monitor 102 connected to the signal processing device 4, for displaying the video signal, and a still camera device 103 which is mounted on a monitor image plane of the color monitor 102, for film-photographing a monitor image which is displayed on the monitor image plane.

Further, in the present embodiment, a flexibility display-signal generation circuit 88' generates a flexibility display signal which displays a flexibility level on a position within the endoscope image display region 5a on the side of periphery thereof, or the like. Specifically, a flexibility display signal is outputted during a period of time during which the endoscope image exists, with respect to the video signal which is outputted from the signal processing circuit 25. In this case, as shown in FIG. 13, the flexibility display region 5b is presented in an endoscope image display region 5a, and the detected flexibility is displayed on the flexibility display region 5b.

The arrangement is as follows. That is, if, in order to observe the endoscope image display region 5a, the operator observes this region 5a, the flexibility level also naturally enters the eyes when viewing region 5a. Accordingly, it is possible to know a set flexibility level.

The still camera 103 is arranged such that a photographing lens 104 is disposed in opposed relation to the monitor image plane, and a film 105 is disposed at an imaging position thereof. Moreover, a shutter 106 is disposed between the photographing lens 104 and the film 105, and is opened and closed by a shutter drive mechanism 107.

The shutter drive mechanism 107 is so arranged that an operation thereof is controlled by a drive control circuit 108. The drive control circuit 108 is connected to a release switch 109. If a release signal which indicates release is inputted by switch operation of the release switch 109, the drive control circuit 108 generates a corresponding second drive control signal, to open the shutter 106 through the shutter drive mechanism 107 for a short period of time.

Further, the first drive control signal which is outputted from the drive control circuit 108 is applied to a control end of an analog switch 110 which is provided between an output end of the flexibility display-signal generation circuit 88' and the mixer 89 within the signal processing device 4. When the release signal is inputted, prior to the fact that the shutter drive mechanism 107 is driven (before 1 frame period of time, for example), the analog switch 110 is turned OFF for a short period of time, and a memory (not shown) of the signal processing circuit 25 is set to a writing inhibit state for a short period of time. During the period of time, a still image is displayed.

If the analog switch 110 is turned OFF, since a signal which displays flexibility is not outputted, only the endoscope image is displayed on the endoscope image display region 5*a*, and an endoscope image thereof is photographed in film.

Figure 14A:
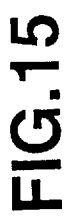
FIG. 14A is a perspective view showing a torus.
Figure 14B:
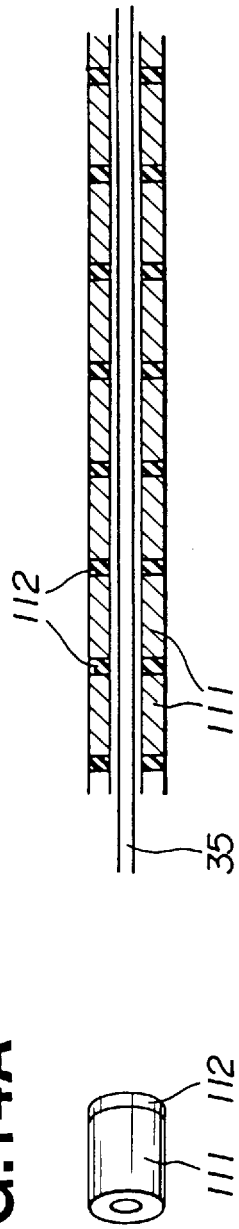

Further, the electronic endoscope 2 according to the present embodiment employs an arrangement in which tori 111 are linked together, in place of the coil 36 which is formed such that a wire is wound spirally. For example, the wires 35 as shown in FIG. 14A pass respectively through the tori 111 as shown in FIG. 14B so that the flexibility variable member is formed.

The tori 111 are made of, for example, stainless steel or the like. A member which has elasticity such as a ring 112 made of rubber, or the like, is firmly fixed or mounted to one end part of each of the tori 111 by adhesives or the like.

Under a state in which the wire 35 is not pulled, the adjacent tori 111 are under a state in which they are loosely in contact with each other through the ring 112 therebetween. Under this state, the tori 111 which are adjacent each other at portions of the ring 112 therebetween are a soft state which becomes bendable. The adjacent rings 112 are compressed by the fact that the wire 35 is pulled, so that the adjacent tori 111 can be set to a state difficult to be bent, that is, to a state in which flexibility is small and they are hard.

The other is substantially similar to the electronic endoscope according to the first embodiment. For example, the wire 35 has a forward end thereof which is fixed to the connection pipe 38. At a position slightly more rearward than that position, the torus 111 at the most forward end is fixed to the wire 35. Moreover, the torus 111 at the most rearward end is such that movement thereof toward the rearward side is regulated by the coil stopper 40 (refer to FIG. 2). The wire 35 which passes through the respective tori 111 extends rearwardly from the coil stopper 40.

Operation of photographing in film in the present embodiment will first be described. Under a state in which the release switch 109 is not operated, the detected flexibility within the endoscope image display region 5*a* is displayed on the display surfaces of the color monitors 5 and 102, as shown in FIG. 13.

If, under this state, the release switch 109 is operated, the release signal is inputted to the drive control circuit 108 so that corresponding first and second drive control signals are generated. First, as the first drive control signal, a signal of the "H", for example, is applied to the signal processing circuit 25 and the analog switch 10. The video signal which is outputted from the signal processing circuit 25 becomes one which corresponds to the still image, and the analog switch 110 is turned OFF. Thus, the state is made to a state in which the flexibility is not displayed within the endoscope image display region 5*a*.

The second drive control signal which is outputted subsequently (after a degree of a 1 frame period of time) is inputted to the shutter drive mechanism 107 to change it to an operative state, to close the shutter 106 after it is opened for a short period of time (few frame periods of time, for example). By the fact that the shutter 106 opens, an endoscope image which is displayed on the monitor image plane, or the like, is image-formed on the film 103 by the photographing lens 104. The film 103 is exposed by this image-formation. In this case, the endoscope image is photographed under a state in which the flexibility is not displayed. Since, when a diagnosis is performed by photographs, display of the level of the flexibility, or the like, is unnecessary, the arrangement is such that photographing is performed under a state in which the flexibility is not displayed.

After the shutter 106 has been closed, the drive control circuit 108 changes the first drive control signal to "L" to change it to a writable state, to thereby cancel the still image such that a moving image is displayed, and to turn the analog switch 110 ON to change the state to a state in which the flexibility is displayed.

Moreover, by the fact that such operation as to rotate the flexibility adjustment knob 34 is performed, the rearward end of the wire 35 is moved rearwardly, whereby the length of the wire 35 which projects rearwardly from the coil stopper 40 is increased. Thus, such a compressive force as to press the most rearward torus 111 forwardly is given to the torus column, relatively through the coil stopper 40, making it possible to reduce the flexibility of the torus column.

Specifically, it is possible to variably set the flexibility by function substantially similar or almost similar to case which uses the coil 36.

The present embodiment has function and advantages substantially similar to those of the apparatus 1B in FIG. 11, other than the fact of being provided with a function to perform film photographing.

In connection with the above, the present embodiment uses the torus column. It is possible, however, to use a spiral pipe 117 which is employed in an embodiment to be described later, in place thereof. In this case, the spiral pipe 117 has an inner diameter thereof which is a degree of an inner diameter of the torus 111 which is capable of being inserted into and passing through the wire 35.

Figure 15:
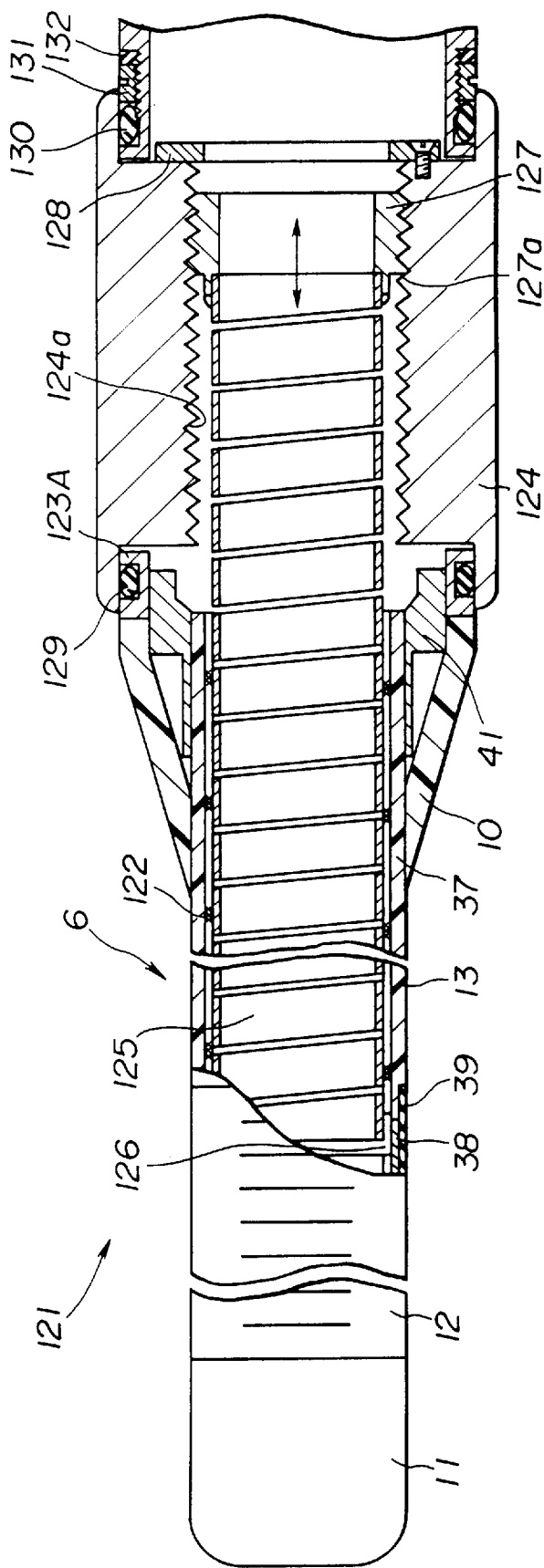
FIG. 15 is a cross-sectional view showing a brief arrangement of a flexibility adjustment mechanism in an endoscope according to an eighth embodiment of the present invention.

FIG. 15 shows a flexibility adjustment mechanism in an endoscope 121 according to an eighth embodiment of the present invention. A mesh pipe 122 in which a thin wire is made into a net is arranged within the flexible pipe 37 which forms the flexible part 13.

The flexible pipe 37 and the mesh pipe 122 have rearward ends thereof which are fixed to the base 41 within the failure prevention member 10 in the form of a taper, which is provided at the connection part between the operation part 7 and the same. A first cylindrical pipe 123A which is formed by the operation part 7 is fixed to the rearward end of the base 41, which is enlarged in diameter. A flexibility adjustment knob 124 is rotatably arranged or disposed between the rearward end of the first cylindrical pipe 123A and a second cylindrical pipe 123B which is disposed in the rear thereof.

A spiral pipe (flex) 125 which forms the flexibility modification member is disposed within the mesh pipe 122.

The spiral pipe 125 is a pipe in which a metal in the form of a belt is wound spirally, and has a slight gap with respect to the adjacent portion. The spiral pipe 125 has a forward end thereof which is fixed, by a silver solder 126, to the connection pipe 38 by the fact that the net of the mesh pipe 122 passes therethrough, or the like.

Further, the spiral pipe 125 extends to the side more rearward than the rearward end of the flexible pipe 37. The spiral pipe 125 has a rearward end thereof to which a substantially cylindrical moving member 127 is fixed by brazing or the like. The moving member 127 has an outer peripheral surface thereof on which a male thread 127*a* is formed. The male thread 127*a* is engaged in a threaded manner with a female thread 124*a* which is formed in an inner peripheral surface of the flexibility adjustment knob 124.

Accordingly, such operation as to rotate the flexibility adjustment knob 124 is performed whereby it is possible to move the moving member 127 in a direction indicated by arrows, in accordance with an orientation or a direction of the rotation. For example, the moving member 127 is moved forwardly, whereby the compressive force is applied from the rearward side to the spiral pipe 125 by the moving member 127. The compressive force is applied to portions which put therebetween a small gap. Thus, setting is made to a state which is difficult to be bent and in which the flexibility is small.

Furthermore, a coming-out prevention member 128 in the form of a ring is fixed, by a screw, to the rearward end of the flexibility adjustment knob 124, to perform function of coming-out prevention when the moving member 127 is moving rearward.

Further, the flexibility adjustment knob 124 has a forward end and a rearward end thereof which are cut away and which are fitted respectively over outer peripheral surfaces of the first cylindrical pipe 123A and the second cylindrical pipe 123B. Peripheral grooves are formed respectively in the fitting portions, and O-rings 129 and 130 are received therein, respectively.

These O-rings 129 and 130 have a function to make, when the flexibility adjustment knob 124 is provided, an interior thereof to a water-tight structure and, in addition thereto, have also function to make the same to a structure in which a frictional force always acts between the first cylindrical pipe 123A and the second cylindrical pipe 123B, and the flexibility adjustment knob 124, to lock the flexibility adjustment knob 124.

Specifically, it has function of, even if, under a state in which the flexibility adjustment knob 124 is rotatively operated by a hand, the hand is removed from the flexibility adjustment knob 124, locking the flexibility adjustment knob 124 to the state, whereby the flexibility of the spiral pipe 125 is locked to the flexibility state which corresponds to the flexibility adjustment knob 124 and the moving member 127 under this state.

In the present embodiment, the flexibility adjustment knob 124 which serves as the flexibility operation member is rotatively operated, without the use of the wire 35 in the first embodiment, whereby it is possible to compress the spiral pipe 125 through the moving member 127 to change the flexibility thereof.

Moreover, in the present embodiment, the peripheral groove in which the O-ring 130 is received, for example, has a rearward end thereof which is in communication with the threaded part, a ring 131 which is provided on the inner peripheral surface with a screw which is threadedly engaged with the threaded part is threadedly engaged therewith, and, furthermore, a ring 132 which is made of an elastic body, for blasting the ring 131 forwardly, is received. The arrangement is such that recesses are formed respectively at two opposed locations or the like, for example, of the outer peripheral surface of the ring 130, and a jig (not shown) has a projecting piece which is fitted into a recess to angularly move the ring 131, whereby it is possible that the O-ring 130 is pressed to change the magnitude of the frictional force which is applied to the flexibility adjustment knob 124. In other words, the arrangement is such that it is possible to adjust a force to lock the flexibility of the spiral pipe 125.

In connection with the above, the ring 132 prevents the ring 131 from being shifted from the set position of the ring 131 toward a rearward position.

In this manner, the means is provided for adjusting the magnitude of the frictional force, whereby, when the frictional force to lock the flexibility adjustment knob 124 to an optional position is insufficient by secular change or the like, the ring 131 is moved forwardly whereby it is possible to increase the frictional force. Moreover, also when there is variation in the frictional force or the like of each of each endoscope, it is possible to adjust the frictional force. Thus, it is possible to lock the same to an optional flexibility state.

In connection with the above, in the above-described embodiment, the spiral pipe 125 has been used as the flexibility modification member. In place of the same, however, the cylindrical pipe 111 may be employed, which is shown in FIG. 14A. In this case, an arrangement is used in which the cylindrical pipe 111 has the outer diameter thereof which is substantially fitted in the inner diameter of the mesh pipe 122.

The present embodiment has advantages substantially similar to those of the first embodiment.

In connection with the above, when the flexibility adjustment knob for adjusting the flexibility, or the like, is so operated as to reduce the flexibility, the present invention includes an arrangement which is provided with a mechanism which is capable of performing locking of at least one to a hard state which is at least smaller than the state in which the flexibility is the largest.

Moreover, the condition is that, since the present invention has an object to improve the insertion operability, the operation member such as the flexibility adjustment knob or the like is provided on the operation part. If there is the flexibility adjustment member at the periphery other than the operation part, the operator displaces the operation part from his or her hand, or largely changes an insertion attitude or an insertion posture to adjust the flexibility. This remarkably reduces the insertion operability.

Furthermore, the above-described embodiments or the like are so arranged that the operation to modify the flexibility is manually operated. The arrangement, however, may be such a stricture that a motor or the like is driven by operation of a switch or the like to pull the wire 35, and a compressive force is applied to the coil 36 by the traction to modify the flexibility of the flexible part 13. In that case, the arrangement is such that, if the switch is pushed to harden the flexible part 13, even if a finger is left from the switch, it is locked to a hardened state.

Further, the arrangement may be such that, by the fact that the wire 35 is pulled whereby, in place of the fact that the compressive force is applied to the coil 36, the wire 35 or the like is pulled, whereby a force to expand the coil 36 is added to modify the flexibility of the flexible part 13. Moreover, the arrangement may form such a mechanism that, other than the coil 36, a resilient or elastic member or the like in which the flexibility thereof varies in accordance with compression or expansion is used to modify the flexibility. Furthermore, the arrangement may be such that, by the change of phase (structural change) of the shape memory member or the like, the flexibility thereof is changed or modified to modify the flexibility of the flexible part 13.

Next, FIGS. 16 to 20C are referred to, to describe a ninth embodiment of the present invention.

Figure 16:
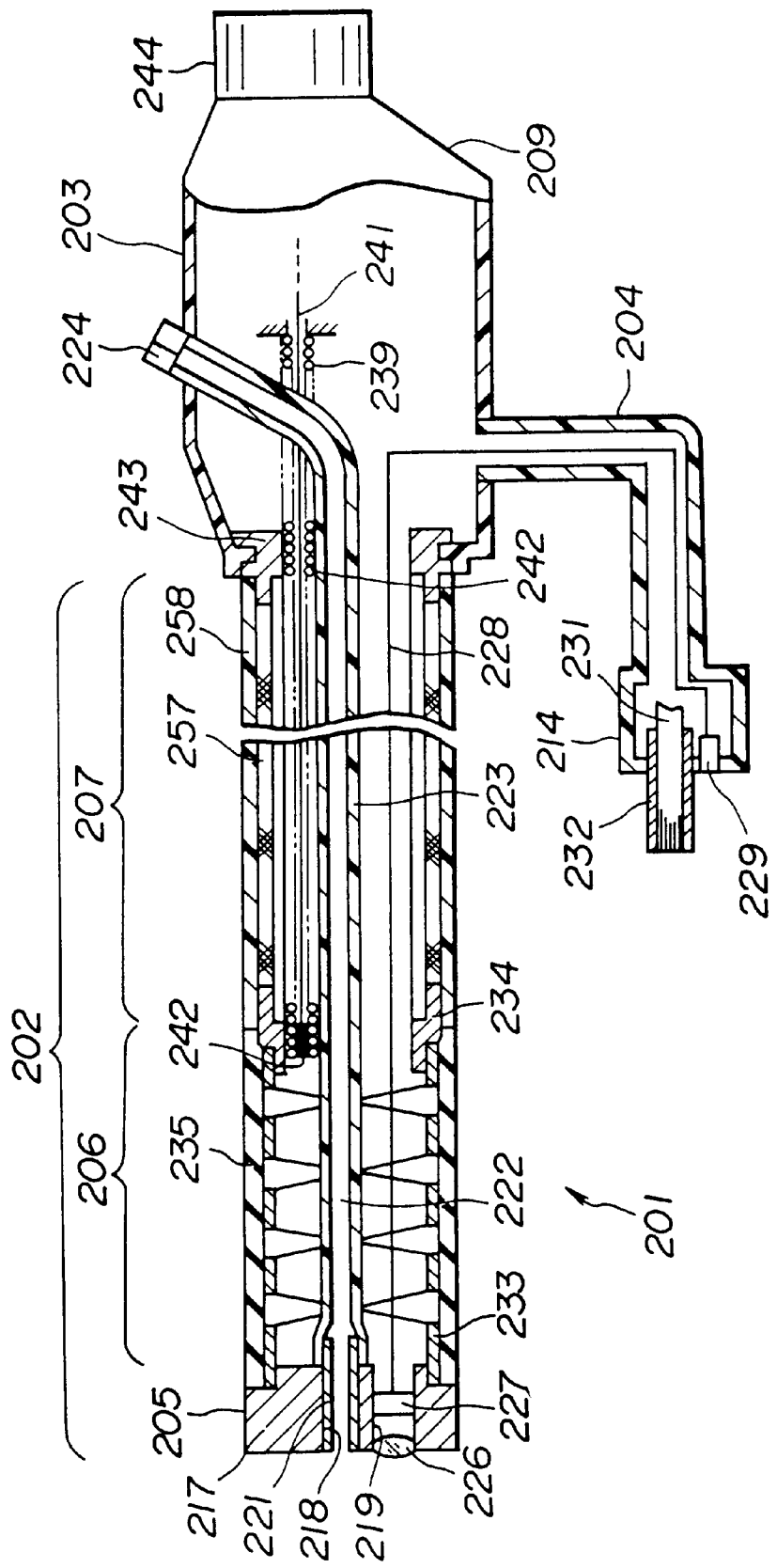

FIG. 16 shows an electronic endoscope 201. The electronic endoscope 201 comprises an elongated flexible insertion part 202, an operation part 203 which has a large diameter and which is connected to the side of a rearward end of the insertion part 202, and a universal cable 204 which extends from the side of the operation part 203.

The insertion part 202 is provided with a rigid forward-end part 205 which is located at the distal end side of the insertion part 202, and is provided with a curve-able curvature part 206 at the rearward side thereof which is adjacent the forward-end part 205. Moreover, a flexible part 207 which has a flexible tubular body is connected to the rearward side of the curvature part 206. The curvature part 206 is so arranged that the curvature operation knob (refer to the reference numeral 208 in FIG. 21) which is provided on the operation part 203 is operated to thereby be curve-able in directions including the top and bottom/the right and left.

A connector (not shown) for being connected to a control device (not shown similarly) which comprises a light source part and a signal processing part for processing the image signal is provided at an extended forward end of the universal cable 204. A monitor (not shown) is connected to the control device.

As shown in FIG. 16, a forward-end part body 217 which is formed in a substantially cylindrical shape from a hard material is provided at the forward-end part 205 of the insertion part 202. A forceps-channel through hole 218 and an observation through hole 219 are provided in parallel with a longitudinal direction of the insertion part 202, in the forward-end part body 217.

A connection pipe 221 is built in the forceps-channel through hole 218. A flexible tube 223 for forming a forceps channel 222 has a forward end thereof which is connected to a rearward part extending rearward of the forward-end part body 217, of the connection pipe 221. The forceps-channel tube 223 is inserted into and passes through the interior of the insertion part 202, and is connected such that a rearward end thereof is led into the operation part 203 and is in communication with a forceps port 224 which is provided in the operation part 203.

An objective lens system 226 is provided in a forward part of the observation through hole 219. A solid-state image pickup component or element 227 is provided at an imaging position of the objective lens system 226. A signal line 228 which is capable of sending an image signal is connected to the solid-state image pickup element 227. The signal line 228 is so arranged as to be inserted into and pass through the interior of the insertion part 202 and as to be connected to a connection contact which is provided on the connector of the universal cable 204, through the operation part 203 and the interior of the universal cable 204.

In connection with the above, a light guide connector 232 which enables the illumination light which is outputted from a light source part (not shown), to be inputted to an end part of the light guide 231 is provided on the connector. The light guide 231 passes through the interior of the universal cable 204, the interior of the operation part 203 and the interior of the insertion part 202, and has a distal end portion thereof which is inserted into a light-guide through hole (not shown) which is provided in the forward-end part body 217. Thus, the arrangement is such that the illumination light can be illuminated to an observation part from the distal end of the light guide 231.

A plurality of articulate frames 233 . . . substantially in the form of a toroid are disposed within the curvature part 206, in a longitudinal direction of the insertion part 202 angularly movably to each other. The most forward articulate frame 233 of the articular frames 233 . . . is so fixed as to be outwardly fitted over a rearward end part of the forward-end part body 217. A toroidal connection part 234 which is provided at the forward end of the flexible part 206 has a forward end part thereof which is fitted over the articular frame 233 at the last end of the plurality of articular frames 233 . . . , and which is fixed thereto.

Further, an angle wire guide which is connected to the rearward end of the forward-end body 217, which is formed by a coil pipe made of a metal and which is not shown in FIG. 16 has a forward end thereof which is connected to the connection pipe 234. A flexible angle wire (not shown) such as a stranded wire or the like which is operated by the curvature operation knob 208 is so inserted into and passes through the interior of the angle wire guide so as to be capable of being pulled and slackened. The arrangement is such that, by the angular operation of the curvature operation knob 208, the curvature part 206 is curved so as to be capable of orienting or directing the forward end part 205 at the forward thereof in the directions including the top and bottom/the right and left. In this connection, the curvature part 206 is covered with a flexible outer skin 235.

By the way, a flexibility adjustment mechanism (means) to be described later is provided in the insertion part 202 so as to be capable of being easily inserted also into the bent or curved body cavity such as a depth part of the large intestine or the like.

Specifically, a coil pipe 239 made of a metal and a traction wire 241 which is inserted into and passes through a lumen or an inner cavity in the coil pipe 239 for performing flexibility adjustment are provided within the flexible part 207 of the insertion part 202, as a flexibility variable member of the flexibility adjustment means. The coil pipe 239 has a forward end thereof which is brazed and fixed, by silver solder 242, to an inner wall of the connection pipe 234 which connects the forward end of the flexible part 207 and the rearward end of the curvature part 206 to each other. Moreover, the flexibility adjustment wire 241 has a forward end thereof which is also fixed to the forward end of the coil pipe 239 or the connection pipe 234 by a silver solder 242 in the same way.

Furthermore, as shown in FIG. 16, the coil pipe 239 has a halfway portion thereof on the side of a rearward end thereof, which is brazed and fixed, by the silver solder 242, to an inner peripheral surface of a connection base 243 which connects the rearward end of the flexible part 207 and the forward end of the operation part 203 to each other. Here, as shown in FIG. 16, the coil pipe 239 has the rearward end thereof which extends up to the interior side of the operation part 203, which is more rearward than the brazing fixing part. In case of FIG. 16, the end part of the coil pipe 239 is fixed to a part of a member of the operation part 203.

In connection with the above, the part of the coil pipe 239 may necessarily be not brazed and fixed to the inner surface of the connection base 243. Further, the forward end of the coil pipe 239 may not necessarily be fixed to the inner wall of the connection pipe 234.

In that case, the coil pipe 239 is unsteady within the insertion part 202. Since, however, it is sufficient not to pull it also together with the connection pipe 234 when the wire 241 is pulled, it is possible to reduce or lighten an operation capacity of the traction wire 241.

Figure 17:
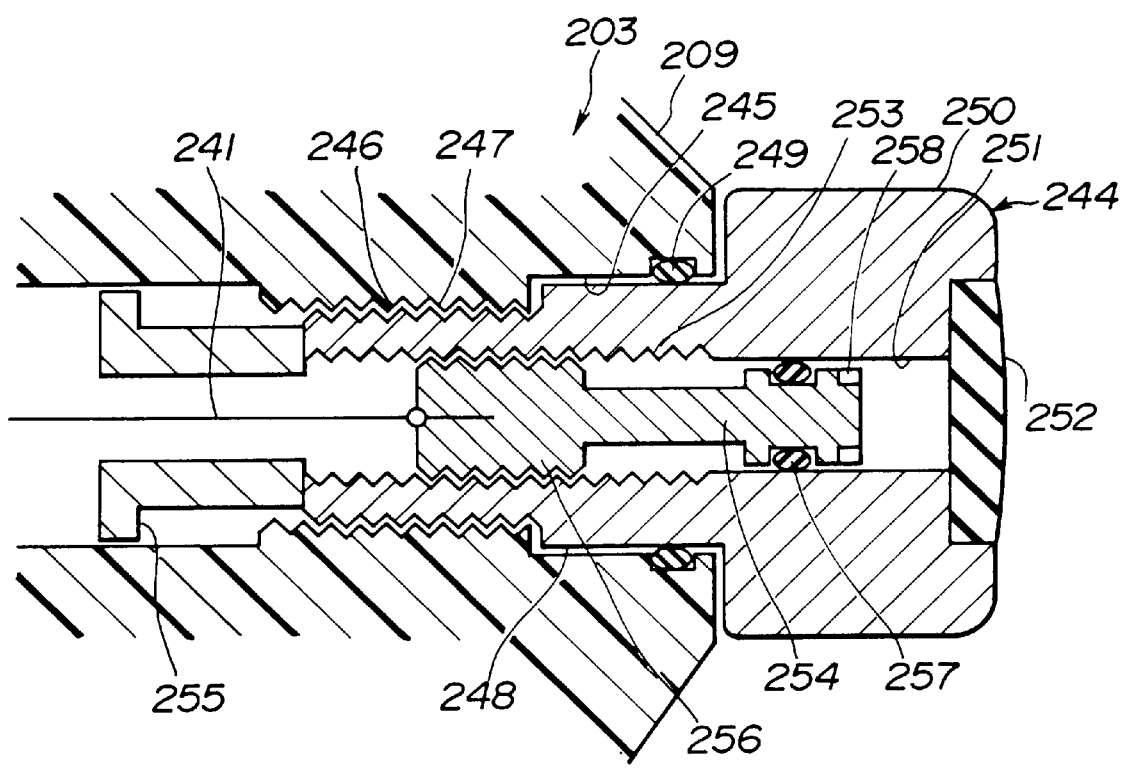

As shown in FIG. 17, the flexibility adjustment mechanism is formed at a portion of the operation part 203 on the side of the rearward end thereof. Specifically, a mounting hole 245 for mounting the flexibility adjustment operation knob 244 is provided in a rear wall of the body 209 of the operation part 203, coaxially with the aforesaid flexibility adjustment member. A female threaded part 246 is formed in an inner end part of the mounting hole 245.

A flexibility adjustment operation knob 244 comprises a tubular member, and a male threaded part 247 which is engaged in a threaded manner with the female threaded part 246 is formed on an outer periphery of an inner end part of the flexibility adjustment operation knob 244. The flexibility adjustment operation knob 244 which is fitted in slide-able manner in the mounting hole 245 has a slide part 248, and an O-ring 249 has function to lock the flexibility adjustment operation knob 244 to an optional operation position by a frictional force thereof.

The flexibility adjustment operation knob 244 has an outer end part thereof which forms a knob 250 thereof. The knob 250 is exposed outside from the rearward wall of the operation part 203.

Incorporated in the flexibility adjustment operation knob 244 is an adjustment mechanism (adjustment means) for returning or restoring tension of the wire 241 in the flexibility adjustment mechanism, to an initial state. Specifically, a rod hole 251 is so formed as to pass through a substantially center part of a member of the flexibility adjustment operation knob 244. The rod hole 251 has an outer end portion thereof which is liquid-tightly filled or closed by a rubber cap 252 which is mounted to the flexibility adjustment operation knob 244. Further, the rod hole 251 has an inner wall thereof a part of which is formed with a female threaded part 253.

Moreover, a rod 254 is fitted and inserted into the rod hole 251. The rod 254 has an inner end part whose outer periphery is formed with a male threaded part 256 which is threadedly engaged with the female threaded part 253 relatively tightly. Furthermore, the rod 254 has an outer end part thereof, and an O-ring 257 is fitted over an outer periphery thereof, to liquid-tightly seal a gap with respect to the rod hole 251. By a frictional force of the O-ring which has elasticity, the rod 254 is fitted in the rod hole 251 relatively tightly. Normally, the flexibility adjustment operation knob 244 and the rod 254 are, in a sense, in such a state as to be united to each other. The arrangement is such that an adjustment hole 258 such as, for example, a pin face hole, is provided in the last end of the rod 254, and, by a tool which conforms thereto, the rod 254 can rotatively be operated.

The flexibility adjustment operation knob 244 has an inner end to which a tubular collar stopper member 255 is mounted and fixed coaxially. The stopper member 255 is moved together with the flexibility adjustment operation knob 244. The stopper member 255, however, forms a mechanism which, when the flexibility adjustment operation knob 244 is moved, impinges, at some point of time, against the forward end of the female threaded part 246 to regulate it such that it is not moved toward the side of hand more than the same.

Moreover, the rod 254 has a forward end thereof to which an end of the traction wire 241 at hand is firmly connected. Thus, when the flexibility adjustment operation knob 244 is turned, function of the female threaded part 246 and the male threaded part 247 causes the flexibility adjustment operation knob 244 to be moved axially. Thus, the arrangement is such that the slide part 248 projects from the rear wall in a body 209 of the operation part 203, in accordance with retraction thereof.

Figure 18:
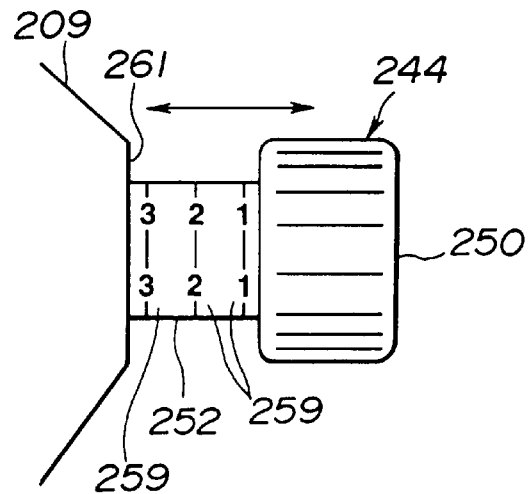

As shown in FIG. 18, a graduation 259 having numbers is provided on an outer periphery of the slide part 248 of the flexibility adjustment operation knob 244. The arrangement is such that, by indication of a graduation 259 in which the rearward wall of the body 209 is made to an index 261, it can know an amount of operation of the flexibility adjustment operation knob 244.

Figure 19A:
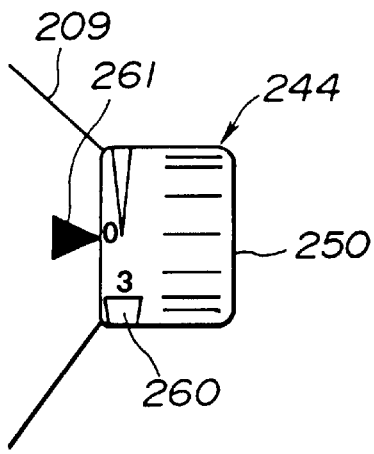
FIGS. 19A and 19B are explanatory views of the other exemplification of the operation portion of the flexibility adjustment mechanism of the endoscope.
Figure 19B:
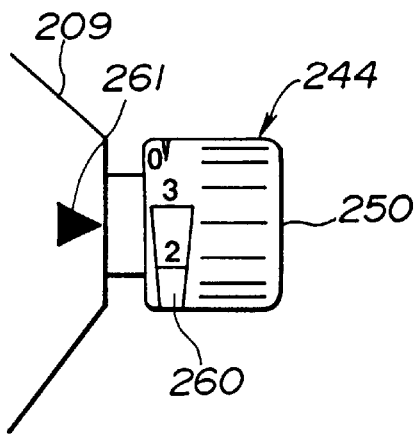

On one hand, FIGS. 19A and 19B show another exemplification in which a graduation 260 is provided on the knob part 250 of the flexibility adjustment operation knob 244. An index 261 is additionally provided in the wall surface of the rearward part in the body 209 of the operation part 203. In such a case, it is possible to read out an amount of rotative operation of the flexibility adjustment operation knob 244 from the graduation 260 and the index 261.

In connection with the above, in case of FIG. 19A or 19B, if the irregularity state on the outer surface of the knob part 250 of the flexibility adjustment operation knob 244 is changed depending upon the rotative position, the touch or feeling of the surface of the flexibility adjustment operation knob 244 with respect to predetermined portions of the index 261 and the body 209 of the operation part 203 is changed in accordance with the flexibility level. Accordingly, it is possible to recognize the adjustment state of the flexibility, by the touch. In this manner, by the fact that the adjustment state can be recognized in a manner of the touch, it is possible to recognize the level of the flexibility under a state in which the user concentrates his or her eyes to the monitor image plane, or even in a dark inspection room.

Further, the arrangement may be such that the graduations 259 and 260, and the index 261 are additionally provided by a fluorescent paint, or are illuminated themselves. With such an arrangement, when the inspection room is darkened, it is easy to view it. Moreover, the graduations 259 and 260 may not be numbers, but may be displayed by figures or graphic forms, kanjis or Chinese characters, and colors. Furthermore, they may be combined with each other.

Next, function of the present embodiment will be described.

Function will be described regarding when the endoscope 201 according to the ninth embodiment is inserted into a large intestine in a manner of oral anus.

Figure 20A:
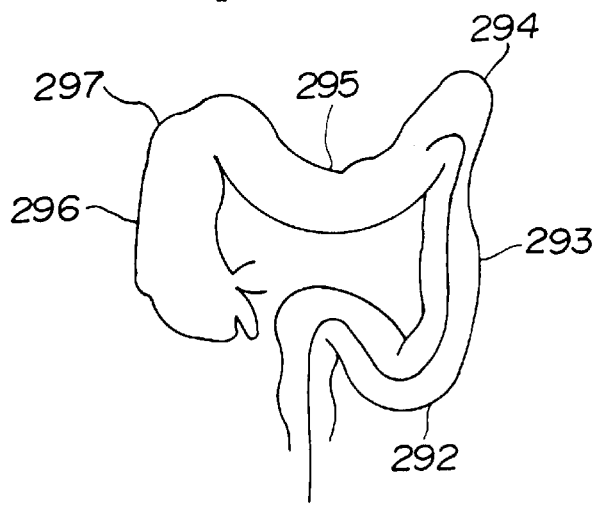
Figure 20B:
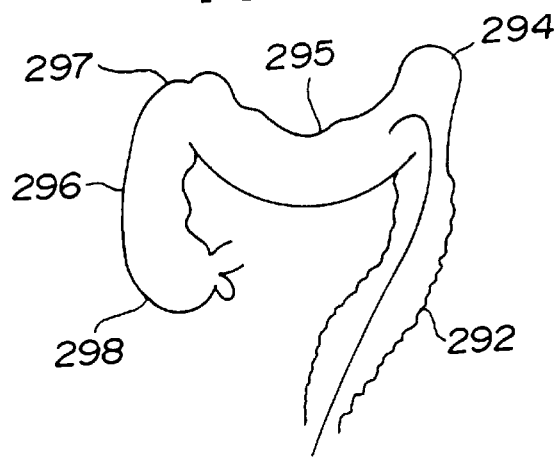

First, the curvature operation knob 208 is operated to insert the insertion part 202 toward the large intestine. As shown in FIG. 20A, after the forward-end part 205 has reached a colon curvature 294 from a lower-line colon 293, the flexible part 207 is twisted while being pulled, to make a curved state of the intestines and the insertion part to a straight state, as shown in FIG. 20B.

Thereafter, if the insertion part 202 is intended to be inserted into a transverse-line colon 295, the vicinity of an S-shaped colon 292 tends to be returned to the curvature state. The flexibility adjustment operation knob 244, however, is angularly moved at the side of hand, whereby it is possible to give the suitable tensile force to the flexibility adjustment wire 241. Thus, the compressive force is given to the coil pipe 239 of the flexibility adjustment means which is within the flexible part 207, whereby the coil pipe 239 is hardened. As a result, since the rigidity of the flexible part 207 can be made large, it is possible to prevent the insertion part 202 from being returned to the curved state. Accordingly, the side of the forward end is curved to smoothly perform insertion to the side of the transverse-line colon 295.

Figure 20C:
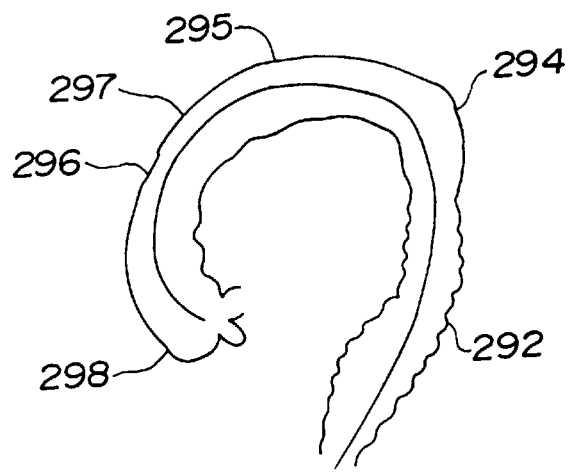

Furthermore, by the fact that the insertion part 202 passes through the transverse-line colon 295 while the rigidity of the flexible part 207 is made large, deflection of the transverse-line colon 295 is released as shown in FIG. 20C, to exceed a liver curvature 297, to thereby insert the insertion part 202 into a caecum 298 from an upper-line colon 296.

Here, when the flexibility adjustment operation knob 244 is moved angularly, the slide part 248 goes out. As shown in FIG. 18, however, the outer periphery of the slide part 248 has the graduation 259 in accordance with the amount of movement thereof. Accordingly, it is possible to view the tensile force of the wire 241, that is, the level of the flexibility of the flexible part 207, by the graduation 259 (display of [3] in FIG. 18) which is appeared at a location in the vicinity of the index 261 which consists of the rearward-end surface of the operation part 203.

As shown in FIG. 19A or 19B, the arrangement may be such that the graduation 260 is rotated together with the flexibility adjustment operation knob 244, and the graduation 260 which is indicated by the index 261 is seen, whereby the flexibility level is understood or seen. Moreover, as shown in FIG. 18, 19A or the like, the arrangement may also be such that the flexibility adjustment operation knob 244 is moved axially in accordance with the flexibility adjustment level, and the user is in touch with the same, whereby the user knows the position of the knob 244 in a manner of the touch, to recognize the flexibility level.

Next, description will be made regarding when the tensile force or tension of the traction wire 241 in the flexibility adjustment mechanism is adjusted. When the flexibility adjustment operation knob 244 is turned with respect to the operation part 203, the rod 254 which is incorporated therein is also rotated by the frictional resistance due to the O-ring 257 and the frictional resistance of the female thread 253 and the male thread 256, together with the flexibility adjustment operation knob 244. Thereupon, the wire 241 is twisted. However, there is no interference in the flexibility adjustment function.

If the flexibility adjustment operation knob 244 is rotated, and the wire 241 is pulled, however, whereby the adjustment function of the flexibility is repeated, it is usual that the natural length of the wire 241 elongates gradually in view of the durability of the wire 241. If the natural length of the traction wire 241 elongates too much, even if the flexibility adjustment operation knob 244 is turned, for example, even if it is operated until the limit at which the stopper member 255 which is fixed to the knob 244 particularly impinges against the forward end of the female threaded part 246, there may occur a case where sufficient elastic adjustment cannot be performed.

In view of the above, if the flexibility adjustment function thereof begins to be degraded, the cap 252 is removed from the knob 244 to open the rod hole 251. By a jig, or the like, which is fitted in the two adjustment holes 258 in the rod 254, the rod 254 is rotated with respect to the flexibility adjustment operation knob 244 under a state in which the knob 244 is fixed. Then, by the functions of the female threaded part 253 and the male threaded part 256, the rod 254 is moved axially with respect to the flexibility adjustment operation knob 244.

In FIG. 17, if it is moved slightly to the right direction, slackening of the traction wire 241 can be eliminated. If the natural length of the wire 241 is slackened, the slackening is dissolved. In this manner, since it is possible to sometime modify a tensioned condition of the wire 241 under an initial state, also after it has been used repeatedly, it is possible to recover the flexibility adjustment function to a superior state. Further, even if operation thereof disassembles the endoscope 201, since the rod 254 can be moved from the outside, operability is good.

Next, a tenth embodiment of the present invention will be described by the use of FIGS. 21 to 23.

Figure 21:
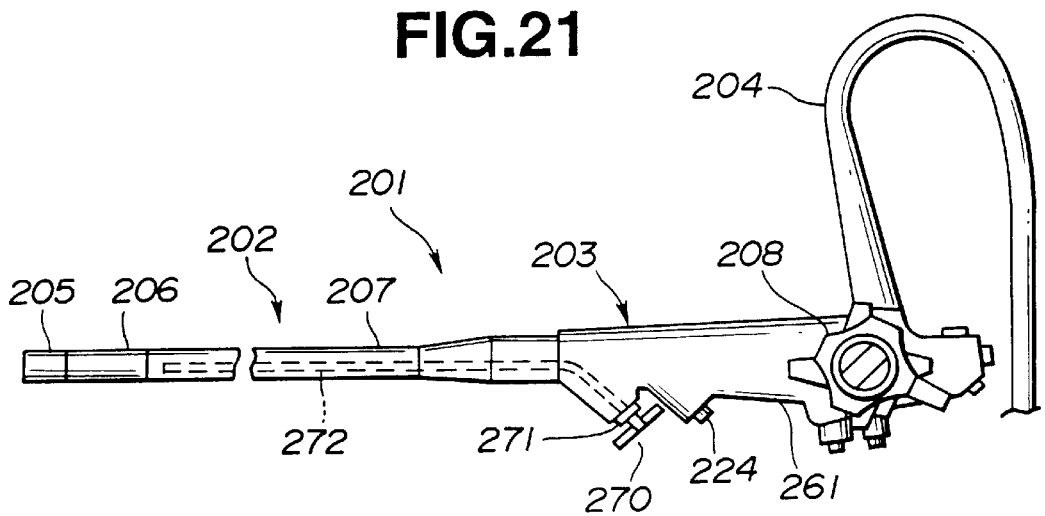
FIGS. 21 to 23 relate to a tenth embodiment of the present invention, FIG. 21 being an explanatory view of a brief arrangement of an endoscope according to the tenth embodiment.
Figure 23:
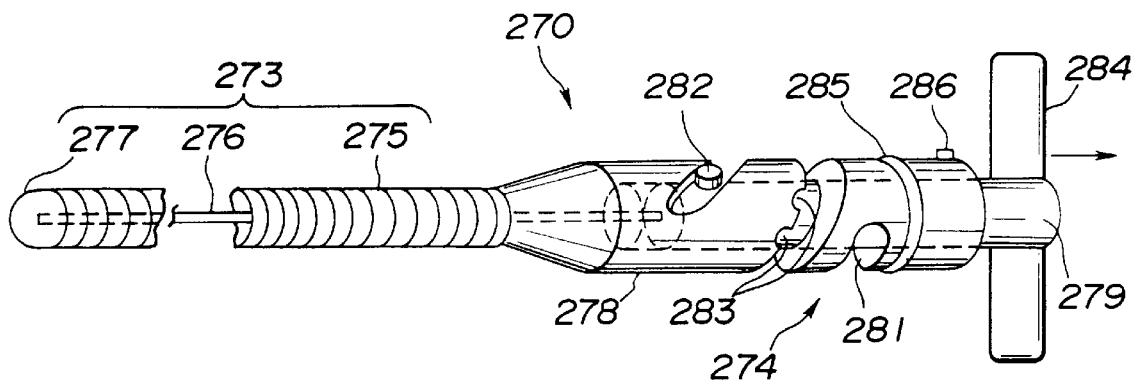

The endoscope 201 according to the present embodiment is provided with an insertion port 271 for inserting and passing the flexibility adjustment device 270 shown in FIG. 23, and an insertion and passing pipe 272 which is in communication with the same, separately from the forceps port 224 and the forceps channel tube 223 as shown in FIG. 21. The insertion and passing pipe 272 has a forward end thereof the side of which is inserted to a location adjacent the forward end of the flexible part 207, and stops on the way of the flexible part 207. A forward end of the insertion and passing pipe 272 is closed liquid-tightly.

As shown in FIG. 23, if largely divided, the flexibility adjustment device 270 has an elongated action part 273 and an operation part 274. The action part 273 has a coil pipe 275 and a traction wire 276 which is inserted into and passes through the same. The wire 276 has a forward-end part thereof which is secured to a forward end 277 of the coil pipe 275. The forward end 277 is finished round so as not to mar the insertion and passing pipe 272.

The coil pipe 275 has a reanvard end thereof which impinges against a body 278 of the operation part 274 and which is connected thereto. The body 278 of the operation part 274 is such that a timbcring or a strut 279 is inserted into and passes through the same in a retractable manner. The wire 276 has a proximal end thereof on the side of a hand, which is connected to the strut 279. A spiral groove 281 in the form of a spiral is provided in the outer peripheral wall part of the body 278.

A pin 282 which is provided on the strut 279 is fitted into the spiral groove 281. Further, the arrangement is such that some recesses 283 (more than one) are provided along the length of the spiral groove 281 so that the pin 282 is fitted into and is engaged with one of the optional recesses 283. A handle 284 is mounted to the rearward end of the strut 279.

Thus, when the handle 284 is angularly moved with respect to the body 278, the pin 282 of the strut 279 is moved along the spiral groove 281. Accordingly, the pin 282 pulls the wire 276 so that it is possible to give the compressive force to the coil pipe 275. Thus, the flexibility of the action part 273 can be changed or varied. By the fact that there are some recesses 283 on the way of the spiral groove 281, the pin 282 is fitted in and is engaged with the recesses 283, whereby it is possible to adjust and hold the flexibility of the action part 273 in a plurality of steps.

The peripheral part of the outer end of the body 278 is provided with a packing 285 and a projection 286 which are fitted in an insertion and passing port 271. The projection 286 is so arranged as to be fitted in a latching groove 287 which is formed in an outer end of the insertion and passing port 271, and as to be engaged therewith.

Figure 22:
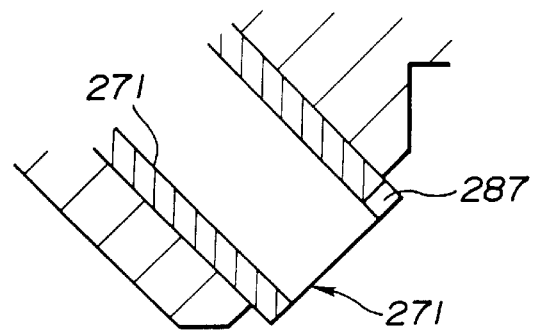

FIG. 22 shows a structure in the vicinity of the insertion and passing port 271 in the endoscope 201. When the flexibility adjustment device 270 is inserted into and passes through the insertion part 202 from the insertion and passing port 271, the packing 285 fixes the flexibility adjustment device 270 to the insertion and passing port 271 by the frictional force while liquid-tightly sealing the insertion and passing pipe 272 in the vicinity of the insertion and passing port 271. Moreover, the projection 286 is fitted into the latching groove 287 in the insertion and passing port 271 and is engaged therewith so that the body 278 of the flexibility adjustment device 270 is mounted so that it will not rotate with respect to the operation part 203.

In connection with the above, although not shown, there is a packing structure also in the inside in the vicinity of the packing 285 of the body 278. Thus, the arrangement is such that the strut 279 is movable liquid-tightly. Accordingly, under a state in which the flexibility adjustment device 270 is mounted to the endoscope 201 as shown in FIG. 21, moisture and filth or dirt are not invaded into the body 278 or into the insertion and passing pipe 272 from the outside, at the time of inspection, at the time of cleaning and at the time of custody. The other structure regarding the endoscope body is the same as that of the aforesaid ninth embodiment.

Next, operation or function of the present embodiment will be described.

As shown in FIG. 21, a state in which the flexibility adjustment device 270 is mounted to the operation part 203 of the endoscope 201 is a fundamental or basic state. Under this state, inspection, cleaning and custody are performed. Since the flexibility adjustment device 270 is mounted so that it does not rotate and maintain a predetermined position in the endoscope 201, one operator has, by one hand, the operation part 203 of the endoscope 201, and can angularly move the handle 284 of the flexibility adjustment device 270 by the other hand so that the flexibility can be adjusted.

The flexibility adjustment is repeatedly performed. If the function of the flexibility adjustment device 270 begins to be degraded or deteriorated by the fact that the natural length of the traction wire 276 is elongated, or the like, the flexibility adjustment device 270 is pulled out together with the unit, and a new flexibility adjustment device 270 is mounted. Since the flexibility adjustment device 270 is pulled out together with the unit, operation thereof is comfortable. It is only the time of exchange that the flexibility adjustment device 270 is removed from the endoscope 201.

Further, even if moisture, dirt or the like enters the insertion and passing pipe 272 during the exchange operation, since the forward end of the insertion and passing pipe 272 is water-tightly closed, the invaded matter does not enter into the internal space of the endoscope 201 from the insertion and passing pipe 272. In this connection, as the case may be, only the traction wire 276 may be exchanged.

The present embodiment has the following advantages.

In the aforementioned embodiment, it is difficult to judge that, if to which position the rod 254 is adjusted, the traction wire 276 is under an appropriately tensile condition. In the present embodiment, however, it is only that the flexibility adjustment device 270 is exchanged for a new flexibility adjustment device 270. Accordingly, it is possible to easily reproduce the appropriate tensile condition of the traction wire 276.

Figure 24:
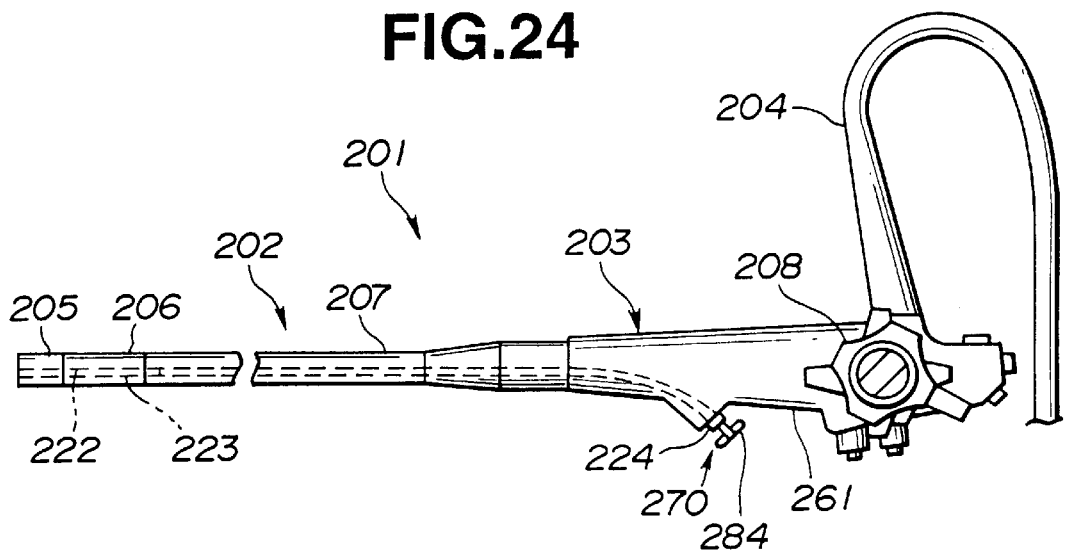
FIG. 24 is an explanatory view of a brief arrangement of an endoscope according to an eleventh embodiment of the present invention.

Next, referring to FIG. 24, an eleventh embodiment of the present invention will be described. In the tenth embodiment, the flexibility adjustment device 270 is provided within the insertion and passing pipe 272 of the endoscope 201. To the contrary, the present embodiment is arranged such that the flexibility adjustment device 270 is inserted into the forceps channel tube 223 which forms the forceps channel 222, from the forceps port 224 in the endoscope 201, and a portion of a handle 284 projects from the forceps port 224.

The arrangement is such that the forceps channel 222 opens at the forward-end part 205, and the forwarded end of the action part 273 of the flexibility adjustment device 270 is positioned adjacent the forward end of the flexible part 207. The other has an arrangement similar to that of the tenth embodiment.

The present embodiment has such advantages as to be applicable to the existing endoscope which has the forceps channel 222. The present embodiment also has other advantages similar to those of the tenth embodiment.

Figure 25:
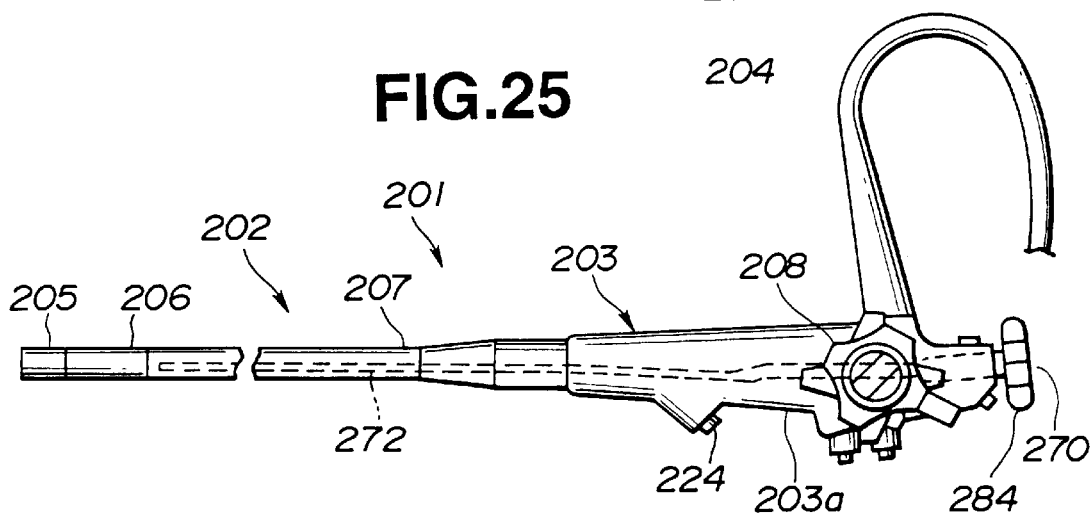
FIGS. 25 and 26 relate to a twelfth embodiment of the present invention, FIG. 25 being an explanatory view of a brief arrangement of an endoscope according to the twelfth embodiment.
Figure 26:
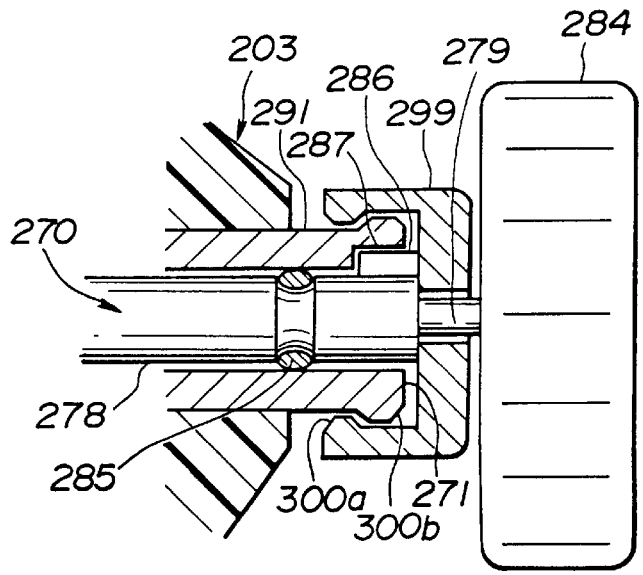

Next, referring to FIGS. 25 and 26, a twelfth embodiment of the present invention will be described.

The arrangement of the preset embodiment is almost the same as that of the aforesaid tenth embodiment. The present embodiment, however, is different from the tenth embodiment in the form or shape of the handle 284 of the flexibility adjustment device 270 and a position at which the flexibility adjustment device 270 is mounted to the endoscope 201. In the present embodiment, the flexibility adjustment device 270 is mounted to the rearward-end part in the operation part 203 of the endoscope 201. A structure in the vicinity of the mounting part is shown in FIG. 26.

A tubular body 291 which is in communication with the insertion and passing pipe 272 is mounted to the rearward end of the operation part 203. On one hand, a lock member 299 which is movable with respect to the strut 279 is provided between the body 278 and the handle 284 of the flexibility adjustment device 270. The lock member 299 has a forward end thereof the side of which is provided with a projection 300a. The tubular body 291 has a rearward end thereof which is provided with a projection 300b. The projections 300a and 300b are in mesh with each other as snap fitting. In this connection, structures of the projection 280 and a latching groove 287 are the same as those in the aforementioned tenth embodiment.

Operation will next be described.

In the arrangement according to the aforementioned tenth embodiment, the axial force by which the flexibility adjustment device 270 is mounted to the endoscope 201 is chiefly only the frictional force of a packing 285. In the present embodiment, however, since the projection 300a of the lock member 299 and the projection 300b of the tubular body 291 are snap-fitted with each other, the flexibility adjustment device 270 is connected to the endoscope 201 by a stronger force.

Accordingly, if a strong force equal to or more than the order which does not occur under the normal use condition is not applied, the flexibility adjustment device 270 does not escape or does not slip out. Accordingly, the flexibility adjustment device 270 does not escape during inspection, during cleaning or the like. Further, meshing between the lock member 292 and the tubular body 291 with each other may not be the snap-fitting, but may be a threaded structure, for example. If so, they can be fixed more firmly. In fact, if it is the snap-fitting, there is a merit that the mounting and the demounting operations are easy.

Moreover, if the flexibility adjustment device 270 is to be mounted to be a part more forwardly (the side of the forward end) than a grip part 203a of the operation part 203, as in the aforesaid tenth embodiment, a portion in front of the grip part 203a is lengthened, and there is a case where it is not easy to handle the insertion part 102. In the present embodiment, however, if it is located on the side of the rearward end further than the grip part 203a, it is possible to shorten a part forward of the grip part 293a. Thus, operability of the insertion part 202 is superior.

According to the present embodiment, there is an advantage that the flexibility adjustment device 270 can finnly be fixed with respect to the endoscope 201. The other has advantages similar to those of the tenth embodiment.

In connection with the above, although common to the aforementioned tenth to twelfth embodiments, the arrangement may be such that the flexibility adjustment device 270 can commonly be mounted on and demounted from also an endoscope of type in which the thickness of the insertion part 202 and the diameter of the treatment-tool insertion and passing channel are different. With such arrangement, the user can use the same flexibility adjustment device 270 can commonly be mounted on and demounted from also an endoscope of type in which the thickness of the insertion part 202 and the diameter of the treatment-tool insertion and passing channel are different. With such arrangement, the user can use the same flexibility adjustment device 270 in different types. Furthermore, the endoscopes which are stored for conversion should be the flexibility adjustment device 270 which has common parts. Thus, handling and administration thereof are easy to be performed.

Figure 27:
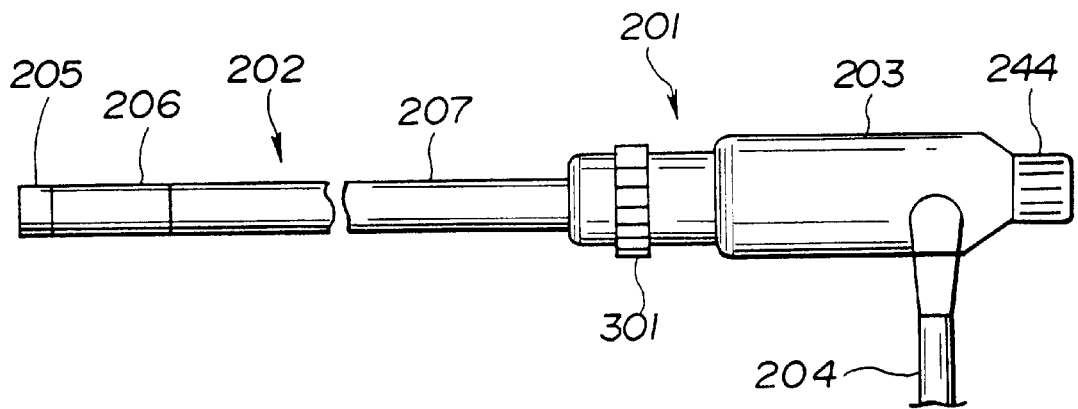
FIGS. 27 and 28 relate to a thirteenth embodiment of the present invention, FIG. 27 being an explanatory view of a brief arrangement of an endoscope according to the thirteenth embodiment.
Figure 28:
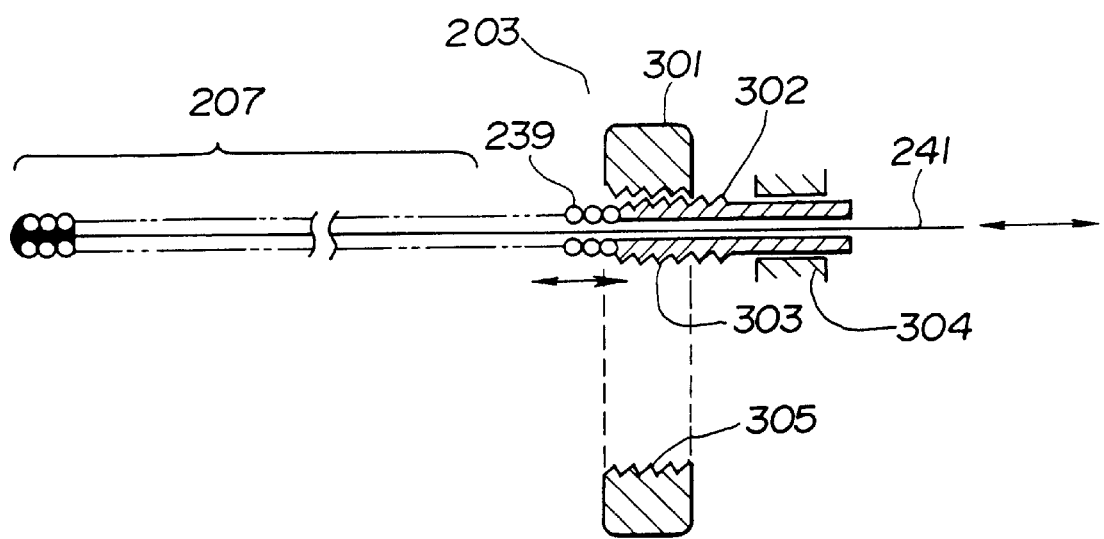

Next, referring to FIGS. 27 and 28, a thirteenth embodiment of the present invention will be described.

The present embodiment corresponds to a modification of the ninth embodiment. Specifically, as shown in FIG. 27, the arrangement is such that a coil adjustment knob 301 for adjusting the tensile condition of the wire 241 of the flexibility adjustment mechanism, from the side of the coil pipe 239 is provided on the forward-end part of the operation part 203 of the endoscope 201. An internal structure thereof is schematically shown in FIG. 28.

The flexible part 207 of the endoscope 201 is provided therein with the coil pipe 239 and the traction wire 241 which is inserted into and passes through the same, similarly to the ninth embodiment. In this connection, a midway portion of the coil pipe 239 is not fixed, but is movable axially. A hollow rod 302 has a forward end thereof which is abutted against the end of the coil pipe 239 at hand. The wire 241 passes through the rod 302, and is movable with respect to the rod 302.

The rod 302 has an outer periphery a part of which is formed with a male threaded part 302. A rearward portion thereof passes through a pedestal 304 which is fixed to the operation part 203. The rearward portion thereof does not rotate with respect thereto, but is movable axially with respect thereto. The coil adjustment knob 301 is provided therewithin with a female threaded part 305 a part of which is in mesh with a part of a male threaded part 303 on the rod 302.

Function will next be described.

In the ninth embodiment, the end of the coil pipe 239 at hand is fixed to the operation part 203. In the present embodiment, however, the coil adjustment knob 301 is angularly moved whereby it is possible to move the rod 302 axially and to move the coil pipe 239 axially. Adjustment of the flexibility of the flexible part 207 is performed by movement of the wire 241 due to the angular movement of the flexibility adjustment operation knob 244, similarly to the ninth embodiment.

It is repeated. When the natural length of the coil pipe 239 is contracted, the rod 302 is moved toward the side in which the coil pipe 239 is compressed, by the coil adjustment knob 301. The relative establishment state between the coil pipe 239 and the wire 241 is altered or modified, whereby it is possible to superiorly secure the flexibility adjustment function. Of course, the arrangement may be such that a mechanism is further added for adjusting the tensile condition of the wire 241 prior to the fact that the flexibility adjustment operation knob 244 is moved, as the ninth embodiment.

Even if the flexibility adjustment function is repeatedly used so that the natural length of the coil pipe 239 is contracted, the tight or close condition of the coil can adequately be adjusted. Accordingly, the present embodiment has such advantages that the flexibility adjustment function can be reproduced under a superior state.

In connection with the above, although it can be said commonly to the aforesaid ninth to the thirteenth embodiments, if the endoscope 201 with the flexibility adjustment function as described above is used, there is the following how to use, other than the fact that the flexibility is changed on the way of insertion into the large intestine, as has been described with reference to FIGS. 20A to 20C.

First, it is beforehand adjusted to the flexibility according to the like of the user to perform inspection. Even in the existing endoscopes, there are types which are different from each other depending upon the difference in hardness of the flexible part, and they are selected on the basis of the like of the user. In the present endoscope 201, however, it is possible to cope with the like of the user only by one.

Further, there is also a case in which even also the same user uses properly types which are different in flexibility from each other in conformance with the individual difference of the large intestines of the patients. In the present endoscope, however, if the flexibility adjustment in accordance with the patents is performed prior to the inspection, it is possible to cope with the individual difference of the large intestines of the various patients, by one.

In connection with the above, according to the ninth to thirteenth embodiments, re-adjustment is performed also after the flexibility adjustment function has repeatedly been used, and recovery or restoration is possible, to enable the original function to be sufficiently exhibited.

Next, referring to FIGS. 29 to 32, a fourteenth embodiment of the present invention will be described.

Figure 29:
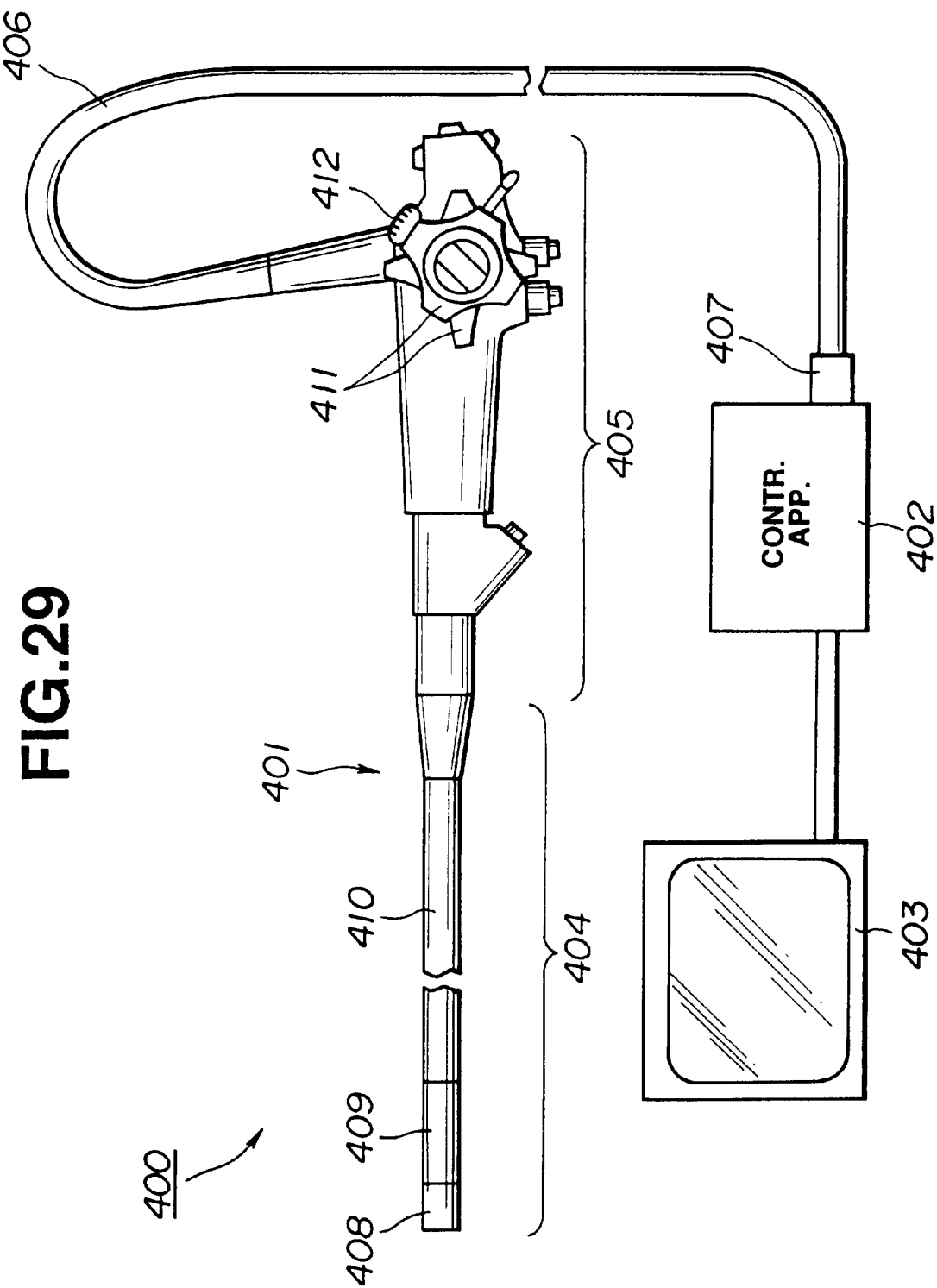

As shown in FIG. 29, an endoscope device 400 is so arranged as to comprise an endoscope 401, a control apparatus 402 having a light source part for supplying an illumination light to the endoscope 401 and a signal processing part for processing, in signal, an image signal which is sent from the endoscope 401, and a monitor 403 for displaying a video signal which is outputted from the control apparatus 402, on an image plane.

The endoscope 401 is so arranged as to comprise an elongated insertion part 404, an operation part 405 large in diameter, which is connected to the side of a rearward end of the insertion part 404, and a universal cable 406 which extends from the side of the operation part 405. A connector 407 is provided at an end of the universal cable 406.

The insertion part 404 is provided with a hard forward-end part 408 at the side of the forward end thereof. At the rearward side thereof adjacent the forward-end part 408, a curve-able curvature part 409 is provided. Further, in rear of the curvature part 409, a flexibility flexible part 410 is connected thereto.

The operation part 405 is provided with a curvature operation knob 411. The arrangement is such that, by the fact that the curvature operation knob 411 is operated. The curvature part 409 can be curved in the directions including the top and bottom/the right and left. Further, a flexibility adjustment knob 412 is provided in the vicinity of the curvature operation knob 411 of the operation part 405. The arrangement is such that flexibility variable means to be described later is operated by the flexibility adjustment knob 412 to alter or change the flexibility of the flexible part 410.

Figure 30:
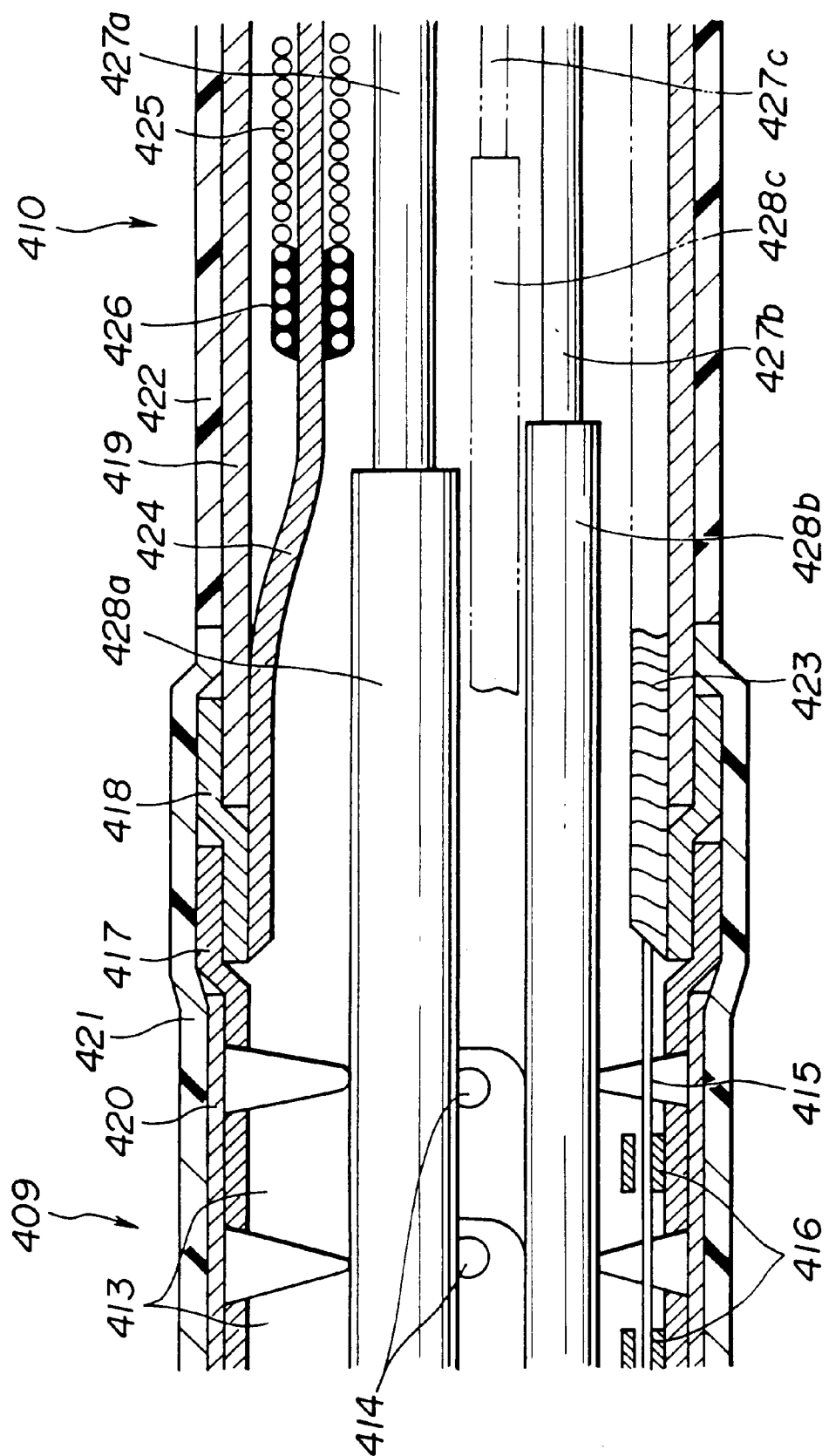

FIG. 30 shows an internal arrangement in the vicinity of a connection part between the curvature part 409 and the flexible part 410 in the insertion part 404.

The curvature part 409 is arranged such that a plurality of generally cylindrical curvature pieces 413 are connected to each other by pins 414 angularly movably. The curvature pieces 413 are provided with wire receipts 416 through which a plurality of curvature wires 415 which are inserted into and pass through the insertion part 404 pass. Each of the curvature wires 415 has a forward end thereof which is connected to and fixed to the curvature piece at the forward end thereof (not shown). The arrangement is such that the curvature wire 415 is pushed and pulled whereby the curvature pieces 413 are moved angularly to curve the curvature part 409 into a desired form so that the forward-end part 408 of the insertion part 404 can be directed in optional directions including the top and bottom/the right and left.

A connection pipe 418 is connected to a rearward-end curvature piece 417 at the rearward end of the curvature part 409 so as to be fitted therein from the rearward end thereof. A bendable or curve-able inner tubular pipe 419 which forms the flexible part 410 has a forward-end part thereof which is fitted into an inner peripheral part at the rearward end of the connection pipe 418, and is connected thereto. A mesh pipe 420 is mounted to an outer periphery of the curvature piece 413 of the curvature part 409. The mesh pipe 420 has an outer periphery thereof which is covered with a cover tube 421. Moreover, an outer periphery of the inner tubular pipe 419 of the flexible part 410 is covered with a skin tube 422.

A coil pipe 423 is arranged within the inner tubular pipe 419. The coil pipe 423 has a forward end thereof which is fixed to the connection pipe 418 by fixing means such as brazing or the like. The curvature wire 415 is inserted into and passes through the coil pipe 423. Further, a flexibility adjustment wire 424 has a forward end thereof which is fixed to the connection pipe 418 by fixing means such as brazing or the like similar to the coil pipe 423.

The flexibility adjustment wire 424 is inserted into and passes through a lumen of a coil pipe 425. The coil pipe 425 has a forward end thereof which is firmly fixed at a halfway fixing part 426 of the flexibility adjustment wire 424. In this connection, at the side of hand further than the fixing part 426 of the flexibility adjustment wire 424, the flexibility adjustment wire 424 and the coil pipe 425 are not fixed, but are free. The flexibility adjustment wire 424 and the coil pipe 425 cooperate with each other to form flexibility variable means.

Visceral objects 427a, 427b and 427c which are arranged within the insertion part 404 are covered respectively with protective tubular bodies 428a, 428b and 428c within the curvature part 409 so that there is no damage or injury such as buckling with respect to bending having small radius of curvature, or the like. These visceral objects 427 (which represent 427a, 427b and 427c) are a signal cable, gas-feeding, water-feeding and suction lines, a channel line and the like which are connected to a light guide or a solid-state image pickup device, for example. In FIG. 30, however, only some of them are shown.

The protective tubular bodies 428 (which represent 428a, 428b and 428c) are formed by a resin tube, a tubular body in the form of a coil, a mesh pipe or the like, for example. The fixing part 426 is provided on the side of hand further than the rearward ends of the protective tubular bodies 428a and 428b. In this connection, in the visceral object 427c, there may be such an arrangement that a rearward end of the protective tubular body 428c is located on the side of hand further than the fixing part 426. Specifically, the arrangement may be such that the fixing part 426 is positioned on the side of hand further than the rearward end of the protective tubular body 428 of at least one visceral object 427, in accordance with an amount of the visceral object 427.

When the protective tubular body 428 is provisionally provided only up to the halfway of the curvature part 409, the fixing part 426 at the forward end of the coil pipe 425 may be positioned within the curvature part 409. The curvature part 409 is, however, bent with a small radius of curvature. When the fixing part 426 and the coil pipe 425 may be is under a hard state, there is a fear that it damages or injures other visceral objects, or destroys the curvature piece 413. For this reason, it is desirable that the fixing part 426 is arranged on the side of hand further than the pin 414 on the most side of hand of the curvature part 409.

Moreover, it is desirable that the rearward end of the protective tubular body 428 and the fixing part 426 are spaced away from each other a distance equal to or more than 5 mm. This is because there is the possibility that the protective tubular body 428 is moved before and behind equal to or more than +/−5 mm by the curvature operation of the curvature part 409. In this connection, when the protective tubular body 428 is moved equal to or more than 5 mm by the curvature operation in relation to the visceral object, the rearward end of the protective tubular body 428 and the fixing part 426 should be spaced apart from the fixing part 426 by a distance corresponding only thereto.

Figure 31:
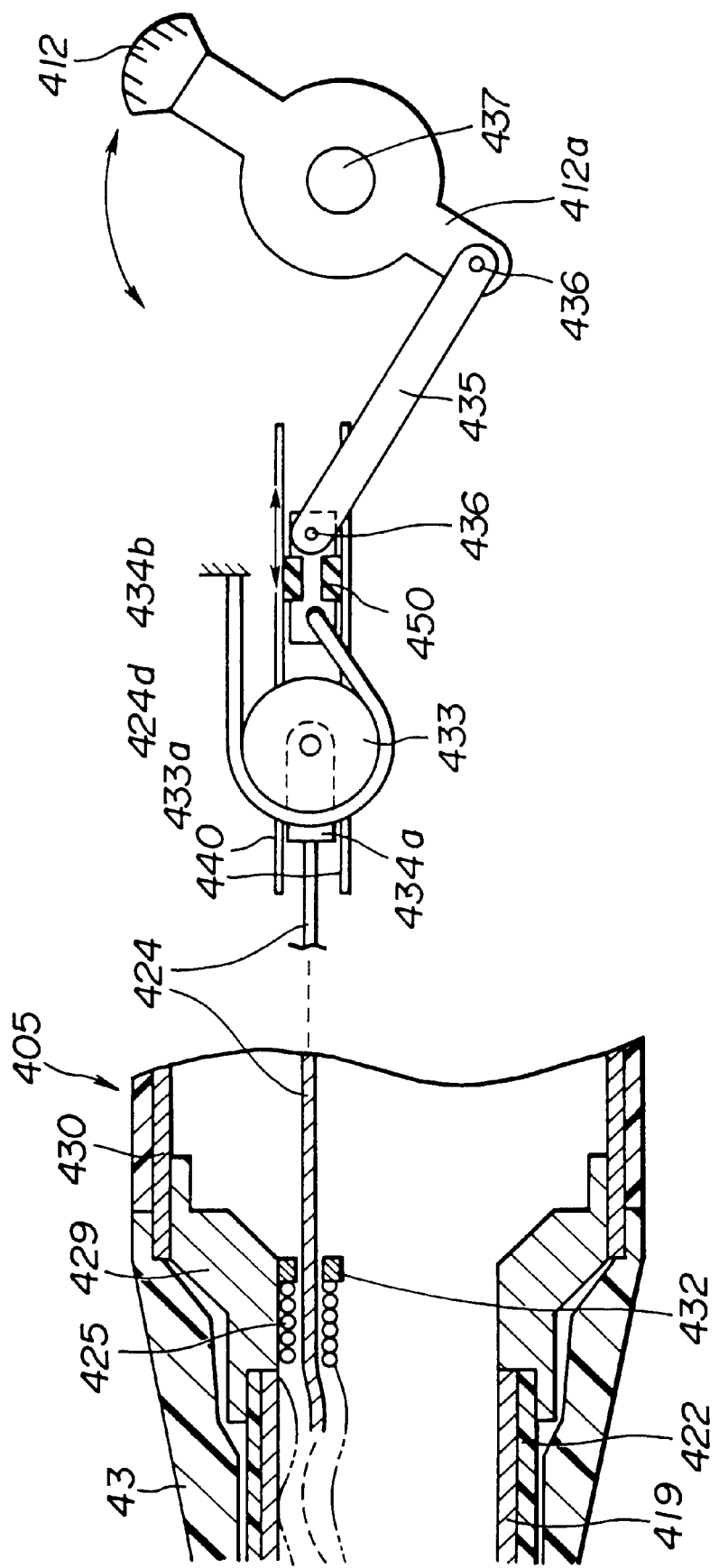

FIG. 31 shows an arrangement of a flexibility adjustment operation mechanism of the flexibility variable means which is provided at the operation part 405.

The outer-skill tube 422 and the inner tubular pipe 419 which form the flexible part 410 of the insertion part 404 have respective proximal ends thereof which are connected to and are fixed to a connection pipe 429 at hand. The connection pipe 429 at hand has a rearward-end part thereof which is mounted to an operation-part body 430. A failure prevention is provided on an outer peripheral part of the connection pipe 429 at hand, specifically, on an outer periphery of the connection part between the insertion part 404 and the operation part 495.

A striking member 432 is mounted on and fixed to an inner peripheral part of the connection pipe 429 at hand. The coil pipe 425 has an end thereof at hand which is abutted against the striking member 432. The flexibility adjustment wire 424 which is inserted into and passes through the interior of the coil pipe 425 passes through a through-hole in the striking member 432, and extends further rearward. The extended flexibility adjustment wire 424 is mounted to one end of a first slide member 434a which is provided within the operation part 405. The other end of the first slide member 434a is mounted to a center shaft 433a of a pulley 433. The pulley 433 is rotatable around the center shaft 433a.

The pulley 433 is provided such that a wire 424a which is different from the flexibility adjustment wire 424 is turned up at the pulley 433. The wire 424a has one end thereof which is fixed by an inner wall of the operation part 405, or the like. The other end of the wire 424a is connected to one end of a second slide member 434b.

The second slide member 434b has the other end thereof to which one end of an arm 435 that is a rod-like member is coinected by the pin 436 and is angularly movably. The other end of the arm 435 is connected to a drive part 412a at the forward end of the flexibility adjustment knob 412, by a pin 436a for angular movement. The flexibility adjustment knob 412 is so provided as to be capable of being rotatively operated around a shaft 437. Furthermore, since the first slide member 434a and the second slide member 434b are so guided as to slide within a guide member 440, the pulley 433, the first slide member 434a and the second slide member 434b slide by the guide member 440 substantially linearly along a direction of the longitudinal axis of the operation part 405.

As shown by the two-dot-and-chain line in FIG. 31, the coil pipe 425 is so arranged as to bump against the striking member 432 under a state in which it is pressed or forced into the flexible part 410 so as to be slightly weaved. When the flexibility adjustment wire 424 is pulled to apply a compressive force to the coil pipe 425, the length of the coil pipe 425 is sligltly shrunk by elastic deformation. Thus, this is an arrangement for absorbing an amount of the shrinkage. In the present embodiment, the arrangement is such that the coil pipe 425 is pressed into the flexible part 410 equal to or more than the amount of shrinkage so that the flexibility adjustment wire 424 does not directly tension or pull the connection pipe 418.

In connection with the above, the rearward end of the coil pipe 425 and the striking member 432 may be arranged so as to be, not only, abutted against each other and latched, but also, fixed against rotation. If the compressive force is applied to the coil pipe 425 by the traction of the flexibility adjustment wire 424, the coil pipe 425 is rotated in such a direction that a diameter thereof is spread. Since, however, the rotation also forms a factor in which the coil length is shrunk, both ends of the coil pipe 425 are so fixed as not to be rotated, whereby it is possible to eliminate shrinkage of the coil pipe 425.

In the arrangement of the present embodiment, when the flexibility adjustment knob 412 is rotatively operated, the first slide member 434a and the pulley 433 slide in a direction of the longitudinal axis of the operation part 405 in interlocking with the flexibility adjustment knob 412, to pull the flexibility adjustment wire 424. At this time, since one end of the wire 424a is passed round the pulley 433 and is fixed to a part of the operation part 405, it is possible to pull the same with a capacity or ability half that by which the flexibility adjustment wire 424 is directly pulled.

When the flexibility adjustment wire 424 is pulled, a compressive force is applied to the outside coil pipe 425. The flexibility of the coil pipe 425 is reduced. As a result, the flexible part 410 is hardened. In this manner, the arrangement is such that the flexibility adjustment knob 412 can be operated to adjust the flexibility of the flexible part 410.

Further, for example, the second slide member 434b is formed, at a center part thereof in the longitudinal direction, with a recess to which a frictional member 450 which has elasticity or resiliency such as rubber or the like is integrally mounted by adhesives. A frictional force acts upon the frictional member 450 when it slides with respect to the guide member 440.

Even if the hand which operates the flexibility adjustment knob 412 is removed from the flexibility adjustment knob 412, the second slide member 434b is locked to the position by the frictional force of the frictional member 450, whereby the set flexibility state can be locked.

Figure 32A:
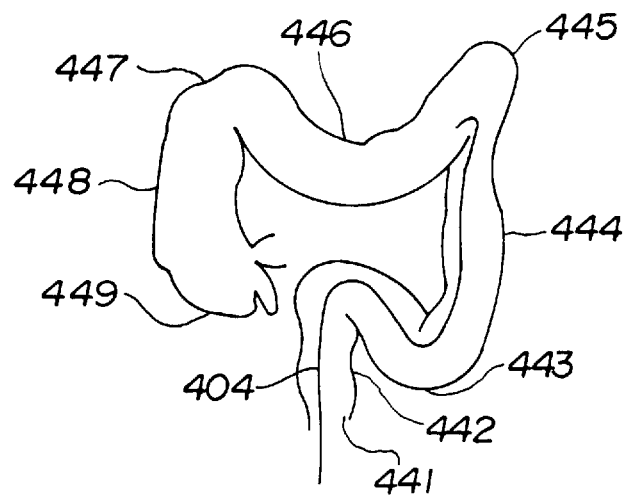

Next, referring to FIGS. 32A to 32C, a function when the insertion part 204 of the endoscope 201 is inserted into a large intestine in an oral anus manner will be described.

First, the flexibility adjustment knob 412 is made to an initial state. Without the fact that the compressive force is applied to the coil pipe 425, under a state in which the flexible part 410 is soft, as shown in FIG. 32A, the insertion part 404 is inserted while being curved from an anus 441 through a rectum 442 substantially along a bent or curved S-shaped colon 443.

At this time, since the flexible part 410 is soft, a pain to a patient can be reduced. If the flexible part 410 is increased in diameter as the arrangement of the prior-art example, the insertion ability will be reduced because the flexible part cannot be made to sufficient softness, and the degree of freedom of the flexible part 410 within the intestines is reduced.

Figure 32B:
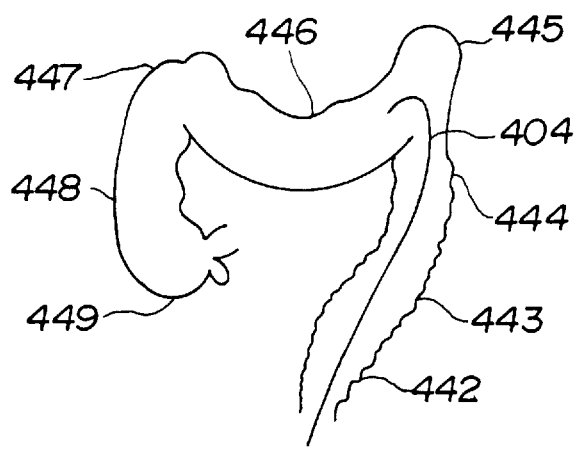
Figure 32C:
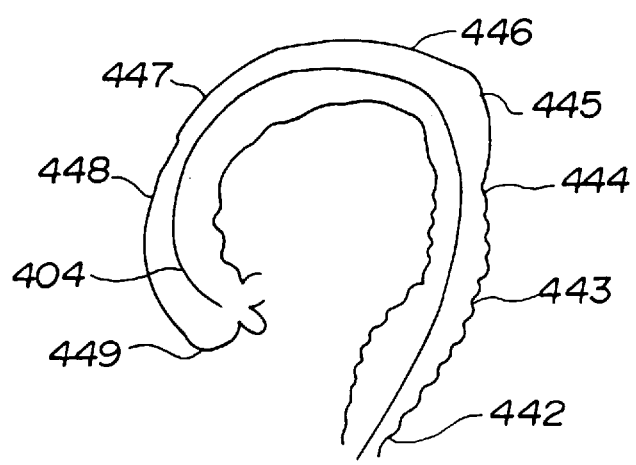

Thereafter, if the forward end of the insertion part 404 is inserted to a location in the vicinity of a splenical curvature part 445 from the S-shaped colon 443 through a lower-line colon 444, as shown in FIG. 32B, the flexible part 410 and the S-shaped colon 443 are substantially straightened so that the side of the insertion part 404 at hand is pulled. At this time, if the flexible part 410 is maintained soft, even if it is tried to insert it to a further depth, the flexible part 410 will be deflected on the way of the flexible part 410 so that the forward end of the insertion part is difficult to go forward.

In view of the above, in a state shown in FIG. 32B, the flexibility adjustment knob 412 is operated to apply the compressive force to the coil pipe 425, to harden the flexible part 410. Under this state, if the insertion part 404 is inserted into the depth, as shown in FIG. 32C, it is possible to insert the insertion part 410 from the splenical curvature part 445 to a transverse colon 446, a liver curvature part 447 and an upper-line colon 448 such that the flexible part 410 describes a large curvature, without the fact that the flexible part 410 is deflected on the way. Thus, it is possible that the forward end of the insertion part 404 easily reaches to a caecum 449.

Within the flexible part 410 and the curvature part 409 of the insertion part 404, at a portion where the protective tubular bodies 428a and 428b are located, the filling rate or ratio of the visceral object is increased, and a state becomes the state in which there is almost no gap. In the present embodiment, at a location where the protective tubular bodies 428a and 428b are present, only the flexibility adjustment wire 424 is provided. The coil pipe 425 is so arranged as to be located on the side of hand further than the rearward ends of the protective tubular bodies 428a and 428b. The coil pipe 425 is arranged at a location where the filling rate of the visceral object is relatively low and there is some gap. Thus, the flexible part 410 is not increased in diameter.

Furtherrnore, since the forward end of the flexibility adjustment wire 424 is fixed to the connection pipe 418, the coil pipe 425 does not twine round the other visceral object to damage that other visceral object due to the fact that the endoscope 401 is repeatedly used. Thus, the visceral object is always kept to a predetermined layout.

In connection with the above, the flexibility adjustment wire 424 and the coil pipe 425 may be formed by super elastic alloy. In this case, since the flexibility adjustment wire 424 and the coil pipe 425 are difficult to be plastically deformed, even if the hardness adjustment operation is repeatedly performed, it is possible to reduce (or eliminate) plastic deformation such as the elongation of the flexibility adjustment wire 424, the shrinkage of the coil pipe 425, or the like. Thus, it is possible to prevent degradation of the function.

As described above, according to the arrangement of the present embodiment, it is possible to provide the flexibility variable means within the insertion part, while preventing, to the utmost, the increase in diameter of the insertion part. Thus, it is possible to adjust the flexibility of the insertion part.

Subsequent fifteenth to seventeenth embodiments show arrangement examples in which the arrangement of the flexibility adjustment wire 424 and the forward-end part of the coil pipe 425 in the flexibility variable means according to the fourteenth embodiment are modified.

Figure 33:
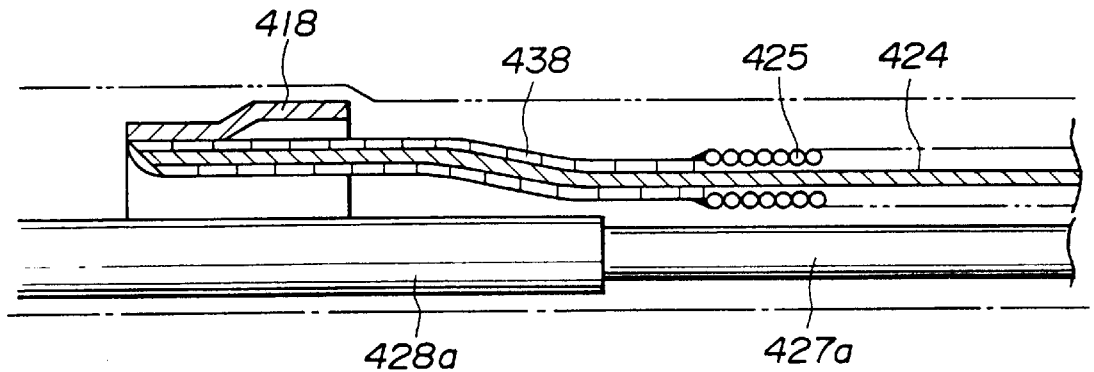
FIG. 33 is a cross-sectional view in an axial direction, showing an arrangement of a principal part of a flexibility variable means in an insertion part of an endoscope according to a fifteenth embodiment of the present invention.
Figure 34:
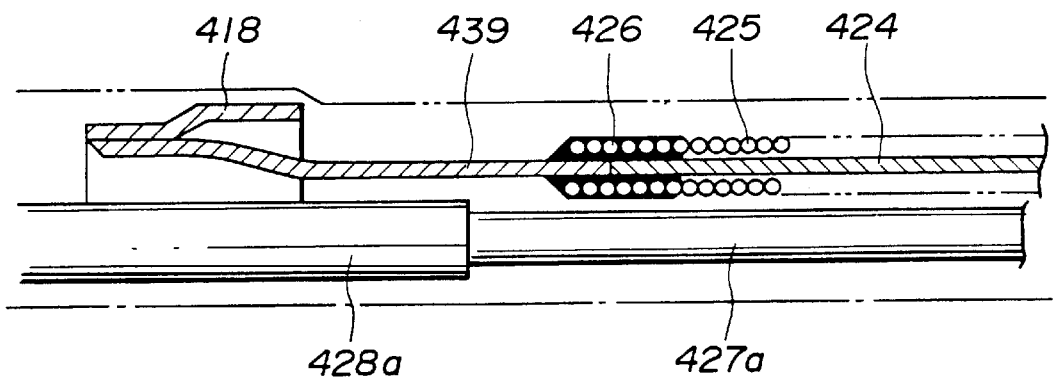
FIG. 34 is a cross-sectional view in an axial direction, showing an arrangement of a principal part of a flexibility variable means in an insertion part of an endoscope according to a sixteenth embodiment of the present invention.
Figure 35:
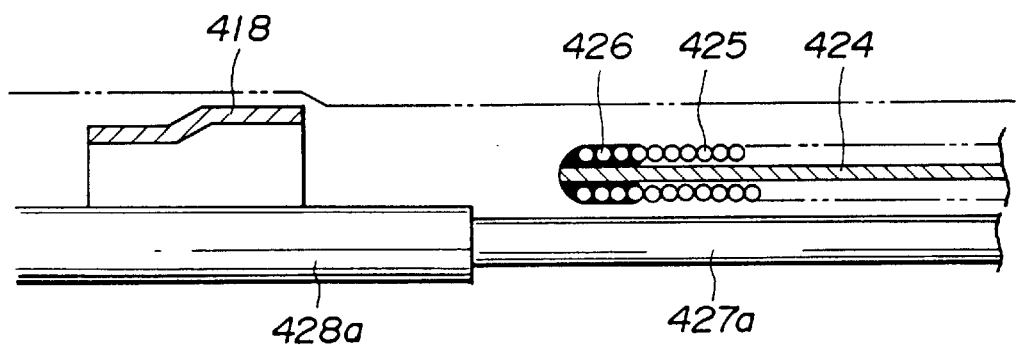
FIG. 35 is a cross-sectional view in an axial direction, showing an arrangement of a principal part of a flexibility variable means in an insertion part of an endoscope according to a seventeenth embodiment of the present invention.

FIGS. 33 to 35 relate to a fifteenth to seventeenth embodiments, respectively. Only portions different from those of the fourteenth embodiment, in the vicinity of the connection part between the curvature part 409 and the flexible part 410 are shown.

As shown in FIG. 33, in the fifteenth embodiment, a connection coil 438 is provided in front of the forward end of the coil pipe 425, the coil pipe 425 and the connection coil 438 are connected and fixed to each other, and the forward end of the connection coil 438 and the forward end of the flexibility adjustment wire 424 are firmly fixed to the connection pipe 418. In this connection, the forward end of the coil pipe 425 is not fixed to the flexibility adjustment wire 424.

The connection pipe 438 is substantially identical in inner diameter with the coil pipe 425, but an outer diameter thereof is formed thin. Further, the connection coil 438 is arranged such that an element wire or a strand whose cross section is not circular, but is a variant or a heteromorphy (rectangle, for example) is wound in the form of a coil. In this connection, the connection coil 438 may be formed by an element wire whose cross-section is circular, similar to the coil pipe 425.

The arrangements of the other portions are similar to those of the fourteenth embodiment and, therefore, the description will be omitted.

In the present embodiment, the connection coil 438 is provided on the side of the forward end of the coil pipe 425, together with the flexibility adjustment wire 424. The connection coil 438 is positioned at a place where the protective tubular bodies 428a and 428b present. The coil pipe 425 is positioned on the side of hand further than the rearward ends of the protective tubular bodies 428a and 428b. Since the connection coil 438 is reduced in diameter less than the coil pipe 425, the flexible part 410 is not increased in diameter.

In the arrangement of the fourteenth embodiment, the flexible part 410 further forward than the forward end of the coil pipe 425 cannot be made to be variable in flexibility. In the fifteenth embodiment, however, since it is possible to apply the compressive force also to the connection coil 438, the connection coil 438 can also be modified or changed in flexibility. Accordingly, it is possible that the flexibility is variable up to the forward end of the flexible part 410. In this case, the flexibility is modified on the way of the flexible part 410.

In connection with the above, since the connection coil 438 is reduced in diameter more than the coil pipe 425, the flexibility when hardened does not extend to the coil pipe 425.

Moreover, when the element wire of the connection coil 438 is circular in cross-section, since a diameter thereof is made smaller than the element wire of the coil pipe 425, there is a fear that the element wires are apt to slip off each other, or contacts between the element wires are apt to be caused or be broken when the compressive force is applied thereto. In the present embodiment, however, by the fact that the element wire has a non-circular (rectangular) cross-section, even if the element wire has a reduced diameter, it is possible to avoid the aforementioned deficiencies.

In connection with the above, the forward end of the coil pipe 425 and the rearward end of the connection coil 438 may only be abutted against each other. However, it is more desirable that they are secured firmly. In this manner, by the fact that the forward end of the connection coil 438 and the rearward end of the coil pipe 425 are so fixed to each other as not to be rotated, even if the compressive force is applied thereto, it is possible to prevent that the connection coil 438 and the coil pipe 425 are rotated and are shrink.

In this manner, according to the arrangement of the fifteenth embodiment, it is possible to obtain advantages that the flexibility thereof is variable over the entire length up to the forward end of the flexible part 410, in addition to the advantages of the fourteenth embodiment. Furthermore, even when the entire flexible part 410 can be hardened as in the present embodiment, it is possible to relieve the pain which is given to the patient, that the side of the forward end thereof is not hardened similarly to that on the side of hand.

In connection with the above, the arrangement may be such that, also in an endoscope of type in which it is not hardened up to the most forward end, the flexibility differs on the way by the fact that the size of the coil (diameter of the element wire of the coil, or the like) varies, or the like, such that the side of the forward end of the coil becomes slightly softer than the side of hand thereof.

Next, referring to FIG. 34, a sixteenth embodiment will be described.

In the sixteenth embodiment, a connection wire material 439 which is separate from the flexibility adjustment wire 424 is connected to and fixed to the forward end of the coil pipe 425, and the forward end of the connection wire material 439 is fixed to the connection pipe 418. Further, the arrangement is such that the flexibility adjustment wire 424 has a forward end thereof which is fixed to the forward end of the coil pipe 425, and the coil pipe 425, the flexibility adjustment wire 424 and the connection wire material 439 are connected and fixed at the fixing part 426.

The connection wire material 439 is formed such that an outer diameter thereof is reduced in diameter less than that of the coil pipe 425. In this connection, the connection wire material 439 may be formed by any of a single-line wire, a pipe material, a coil-like member and the like. Moreover, the connection wire material 439 may be softer than the flexibility adjustment wire 424, or may be harder than the same.

The arrangements of the other portions are similar to those of the fourteenth embodiment and, therefore, the description will be omitted.

In the present embodiment, the connection wire material 439 is provided at the side of the forward end of the coil pipe 425, the connection wire material 439 is positioned at a place where the protective tubular bodies 428a and 428b present, and the coil pipe 425 is positioned at the side of hand further than the rearward ends of the protective tubular bodies 428a and 428b. Since the connection wire material 439 is reduced in diameter less than the coil pipe 425, the flexible part 410 is not increased in diameter.

When the connection wire material 439 is softer than the flexibility adjustment wire 424, it is possible to prevent that the other visceral objects are damaged when the flexible part 410 is curved. On one hand, when the connection wire material 439 is hardened more than the flexibility adjustment wire 424, it is difficult to be twisted. Accordingly, when the compressive force is applied to the coil pipe 425, it is possible to restrain rotation of the coil pipe 425 to eliminate shrinkage due to the elastic deformation and the plastic deformation of the coil pipe 425.

In this manner, according to the arrangement of the sixteenth embodiment, advantages similar to those of the fourteenth embodiment can be obtained. By setting of the flexibility of the connection wire material 439, it is possible to obtain advantages to prevent the other visceral objects from being damaged, or the coil pipe 425 from being shrunk.

Next, referring to FIG. 35, a seventeenth embodiment of the present invention will be described.

The seventeenth embodiment is arranged such that the forward end of the flexibility adjustment wire 424 and the forward end of the coil pipe 425 are fixed at the fixing part 426, and there is no portion which extends toward the forward end more than the fixing part 426. Accordingly, the forward end of the coil pipe 425 is not fixed also to the connection pipe 418, but is under a free state.

The arrangement of the other portions are similar to that of the fourteenth embodiment and, therefore, the description will be omitted.

In the present embodiment, nothing extends to a place where the protective tubular bodies 428a and 428b on the forward-end side further than the fixing part 426 of the coil pipe 425 present. Since the coil pipe 425 is positioned on the side of hand further than the rearward ends of the protective tubular bodies 428a and 428b, the flexible part 410 is not increased in diameter.

Moreover, since the forward end of the coil pipe 425 is free, there is a fear that, during repeated use of the endoscope 401, the coil pipe 425 twines round the other visceral objects. Since, however, assembling operation to fix the forward end of the coil pipe 425 to another member is unnecessary, this is connected to simplification of the assembling operation and reduction of the cost.

In this manner, according to the arrangement of the seventeenth embodiment, such advantages can be obtained that the assembling operation can be simplified, and an attempt can be made to the reduction of the cost, in addition to the advantages of the fourteenth embodiment.

In connection with the above, the flexibility variable means in the fourteenth to seventeenth embodiments is not limited to a combination including the flexibility adjustment wire 424 and the coil pipe 425 as shown in the aforesaid embodiment. Any can be applied if it is an elongated member such as the coil pipe 425. For example, such a shape memory alloy that, when heat is applied, it is straightened hardly, while, when cooled, it is softened may be used. Resin which is hardened by heat may be used.

As described above, according to the fourteenth to the seventeenth embodiments, it is possible to provide the flexibility variable means within the insertion part, without the fact that the insertion part is increased in diameter. Thus, the present invention has such advantages that it is possible to provide the endoscope which is adjustable in the flexibility of the insertion part.

Furthermore, embodiments or the like which are formed by partial combination of the above-described embodiments or the like, or the like, belong to the present invention.

Further, the above-mentioned embodiments or the like have been described with reference to the electronic endoscope in which the image pickup element is arranged at the position in the forward-end part of the insertion part, where the optical image is focused. The present invention, however, includes an optical flexible endoscope which is called "a fiber scope" in which the image pickup element is not used, the optical image is transmitted by a fiber bundle in place thereof, and the transmitted optical image can be observed by the snaked eyes from an eyepiece part.

What is claimed is:

1. An endoscope comprising:

an elongated insertion part provided with a flexible part which has flexibility with respect to bend;

an operation part formed in a vicinity of a proximal end of said insertion part, and provided with a grip for gripping by an operator;

a flexibility varying member arranged within said flexible part, and varying in flexibility with respect to curvature;

a flexibility modifying operation member provided in said operation part, for performing an operation to vary a flexibility of said flexibility varying member; and a notification mechanism for notifying to a user, levels of said flexibility corresponding to the operation of said flexibility modifying operation member.

2. An endoscope according to claim 1, wherein said notification mechanism is a notification mechanism for providing a visual notification to a user.

3. An endoscope according to claim 2 wherein said notification mechanism notifies a level of the flexibility by light emission of a light emitting element.

4. An endoscope according to claim 2, wherein said notification mechanism displays a level of flexibility onto a monitor which displays an endoscope image.

5. An endoscope according to claim 4, wherein said level which is displayed on said monitor is within a given display region of said endoscope image.

6. An endoscope according of claim 4, wherein said level which is displayed on said monitor is outside of a given display region of said endoscope image.

7. An endoscope according to claim 2, wherein, when an image which is displayed on said monitor is photographed on a film, said level which is displayed on said monitor is not photographed.

8. An endoscope according to claim 1, wherein said flexibility modifying operation member is movable and said notification mechanism is a mark which indicates a position occupied by said flexibility modifying operation member, and said mark notifies a level of flexibility of said flexibility varying member which corresponds to a position of said flexibility modifying operation member.

9. An endoscope according to claim 1, wherein said flexibility modifying operation member is a substantially cylindrical-shaped, rotatable operation knob, and said notification mechanism has a surface configuration in a peripheral direction of said operation knob to present different configurations, each representing a different level of flexibility.

10. An endoscope according to claim 1, wherein said flexibility modifying operation member is a substantially cylindrical-shaped, rotatable operation knob, and said notification mechanism indicates a level flexibility of said flexibility varying member from a position in a peripheral direction of a lever, by said lever which extends from said operation knob.

11. An endoscope according to claim 1, comprising a flexibility detection sensor for detecting a value of flexibility of said flexible part.

12. An endoscope according to claim 1, comprising a correction mechanism for correcting levels of said flexibility corresponding to operation of said flexibility modifying operation member.

13. An endoscope according to claim 2 wherein said notification mechanism notifies a level of the flexibility by generating a sound.

14. An endoscope according to claim 13, wherein said notification mechanism generates a click sound.

\* \* \* \* \*

UNITED STATES PATENT AND TRADEMARK OFFICE
CERTIFICATE OF CORRECTION

PATENT NO.    : 5,976,074
DATED         : November 2, 1999
INVENTOR(S)   : Hiroki Moriyama It is certified that error appears in the above-identified patent and that said Letters Patent is hereby corrected as shown below:

In References Cited, before "FOREIGN PATENT DOCUMENTS" please insert:
--5,810,715 09/1998 Moriyama 600/144--

IN THE SPECIFICATION

Column 3,
Line 62, delete the word "clevational" and insert therefor --elevatational--.

Column 22,
Line 37, delete the word "stricture" and insert therefor --structure--.

Column 28,
Line 17, delete the word "reanvard" and insert therefor --rearward--.
Line 20, delete the word "timbcring"and insert therefor --timbering-revolving--.

Column 30,
Line 8, delete the word "rcarward-end" and insert therefor --rearward-end--.

UNITED STATES PATENT AND TRADEMARK OFFICE
CERTIFICATE OF CORRECTION

PATENT NO. : 5,976,074
DATED : November 2, 1999
INVENTOR(S) : Hiroki Moriyama

It is certified that error appears in the above-identified patent and that said Letters Patent is hereby corrected as shown below:

Column 34,
Line 5, delete the word "may be" and insert therefor --per se--.

Column 37,
Line 67, delete the word "shrink" and insert therefor --shrunk--.

Signed and Sealed this

Nineteenth Day of June, 2001

Attest:

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.     : 5,976,074
DATED          : November 2, 1999
INVENTOR(S)    : Hiroki Moriyama It is certified that error appears in the above-identified patent and that said Letters Patent is hereby corrected as shown below:

Title page,
Item [56], References Cited, FOREIGN PATENT DOCUMENTS, please insert:
-- 5,810,715  09/1998  Moriyama  600/144 --

Column 3,
Line 62, delete the word "clevational" and insert therefor -- elevatational --.

Column 22,
Line 37, delete the word "stricture" and insert therefor -- structure --.

Column 28,
Line 17, delete the word "reanvard" and insert therefor -- rearward --.
Line 20, delete the word "timbcring" and insert therefor -- timbering --.

Column 30,
Line 8, delete the word "rcarward-end" and insert therefor -- rearward-end --.

Column 34,
Line 5, delete the word "may be" and insert therefor -- per se --.

Column 37,
Line 67, delete the word "shrink" and insert -- shrunk --.

This certificate supersedes Certificate of Correction issued June 19, 2001.

Signed and Sealed this

Twelfth Day of November, 2002

*Attest:*

*Attesting Officer*

JAMES E. ROGAN
*Director of the United States Patent and Trademark Office*